US011229757B2

(12) United States Patent
Stenzler et al.

(10) Patent No.: US 11,229,757 B2
(45) Date of Patent: Jan. 25, 2022

(54) DRY POWDER INHALERS WITH PARTIAL DOSAGE DELIVERY

(71) Applicant: Philip Morris Products S.A., Neuchatel (CH)

(72) Inventors: Alex Stenzler, Long Beach, CA (US); Steve Han, Huntington Beach, CA (US); Arthur Slutsky, Toronto (CA); Steven Ellis, Oro-medonte (CA); Noe Zamel, Toronto (CA); William Alston, San Jose, CA (US)

(73) Assignee: Philip Morris Products S.A., Neuchâtel (CH)

( * ) Notice: Subject to any disclaimer, the term of this patent is extended or adjusted under 35 U.S.C. 154(b) by 318 days.

(21) Appl. No.: 15/566,372

(22) PCT Filed: Apr. 13, 2016

(86) PCT No.: PCT/US2016/027240

§ 371 (c)(1),
(2) Date: Oct. 13, 2017

(87) PCT Pub. No.: WO2016/168266

PCT Pub. Date: Oct. 20, 2016

(65) Prior Publication Data

US 2018/0093050 A1 Apr. 5, 2018

Related U.S. Application Data

(60) Provisional application No. 62/147,798, filed on Apr. 15, 2015.

(51) Int. Cl.
*A61M 15/00* (2006.01)

(52) U.S. Cl.
CPC .... *A61M 15/0013* (2014.02); *A61M 15/0066* (2014.02); *A61M 15/0021* (2014.02); *A61M 15/0061* (2014.02); *A61M 2202/064* (2013.01)

(58) Field of Classification Search
CPC .......... A61M 15/0013; A61M 15/0021; A61M 15/0061; A61M 2202/064; A61M 15/00; A61M 15/0065–0066
See application file for complete search history.

(56) References Cited

U.S. PATENT DOCUMENTS 2,587,215 A * 2/1952 Priestly ............ A61M 15/0065 128/203.15
4,117,844 A * 10/1978 James ............... A61M 15/0028 128/203.15

(Continued)

FOREIGN PATENT DOCUMENTS

AU 703023 B2 3/1999
JP 2002-165884 A 6/2002

(Continued)

OTHER PUBLICATIONS https://www.merriam-webster.com, Restrict, Accessed Sep. 6, 2021, https://www.merriam-webster.com/dictionary/restrict (Year: 2021).*

(Continued)

*Primary Examiner* — Elliot S Ruddie
(74) *Attorney, Agent, or Firm* — Mueting Raasch Group

(57) ABSTRACT

A dry powder inhaler dispenses a partial dosage of a powder from a dry powder chamber during a single user inhalation. In certain embodiments, the dry powder chamber is a dry powder capsule that spins in a chamber with a protrusion for limiting the spin of the capsule. In certain embodiments, a capsule slides in a proximal and distal direction for dispensing partial dosages of powder medicament. Air inlets in communication whit the external environment can be included in the inhaler housing for generating a smooth inhalation experience for the user and facilitating operation of partial dosage mechanisms. In other embodiments, a hinged member, sliding member, rotating member, spring tensioned member, pressure actuated valve, dry powder (Continued)

chamber with patterned holes or combinations of these are used as a mechanism for dispensing a partial dosage of powder medicament during a single inhalation.

7 Claims, 19 Drawing Sheets

(56) References Cited

U.S. PATENT DOCUMENTS

| | | | | |
|---|---|---|---|---|
| 4,338,931 | A | 7/1982 | Cavazza | |
| 6,234,169 | B1 | 5/2001 | Bulbrook | |
| 7,305,986 | B1 | 12/2007 | Steiner et al. | |
| 7,559,325 | B2 * | 7/2009 | Dunkley | A61M 15/0028 128/203.21 |
| 2004/0149283 | A1 | 8/2004 | Hochrainer | |
| 2004/0206350 | A1 * | 10/2004 | Alston | A61M 15/0033 128/203.12 |
| 2005/0022813 | A1 * | 2/2005 | Alston | A61M 15/0028 128/203.21 |
| 2005/0056280 | A1 | 3/2005 | Alston et al. | |
| 2012/0291781 | A1 * | 11/2012 | Kaufmann | A61M 15/008 128/203.15 |
| 2016/0008557 | A1 | 1/2016 | Smutney et al. | |

FOREIGN PATENT DOCUMENTS

| | | | |
|---|---|---|---|
| RU | 2010143890 | A | 5/2012 |
| RU | 2610779 | C1 | 2/2017 |
| WO | WO 95/03846 | A1 | 2/1995 |
| WO | WO 00/53248 | A1 | 9/2000 |
| WO | WO 03/035137 | A2 | 5/2003 |
| WO | WO 2004/052435 | A1 | 6/2004 |

OTHER PUBLICATIONS https://www.vocabulary.com, Skewed, Accessed Sep. 6, 2021, https://www.vocabulary.com/dictionary/skewed (Year: 2021).*

Russian Office Action and Search Report for RU Application No. 2017136793, including English Translation, dated Aug. 8, 2019; 12 pgs.

Extended European Search Report for EP Application No. 16780602.5, dated May 21, 2019; 15 pgs.

Supplementary Partial European Search Report for EP 16780602.5, dated Feb. 11, 2019, issued by the European Patent Office; 12 pgs.

International Search Report and Written Opinion for PCT/US16/27240, issued by the U.S. Patent Office as the Search Authority, dated Sep. 14, 2016, 11 pgs.

International Preliminary Report on Patentability for PCT/US216/027240, issued by the International Bureau of WIPO, dated Oct. 17, 2017: 8 pgs.

Japanese Office Action issued for JP 2018-0505569 by the Japanese Patent Office, dated Mar. 30, 2020; 10 pgs. including English Abstract.

Chinese Office Action issued for CN 201680032895.4, by the China National Intellectual Property Administration dated Dec. 30, 2019; 15 pgs. including English translation.

* cited by examiner

DRY POWDER INHALERS WITH PARTIAL DOSAGE DELIVERY

CROSS-REFERENCE TO RELATED APPLICATIONS

This application is a national stage entry of PCT/US16/27240, filed Apr. 13, 2016, which claims priority to U.S. provisional application No. 62/147,798 filed on Apr. 15, 2015, both of which are incorporated herein by reference in their entireties.

BACKGROUND OF THE INVENTION

Inhalation of powder nicotine has become an effective and popular way to deliver nicotine to the bloodstream while reducing the hazardous effects of smoking. Unpleasant odors and the hazardous side effects of second hand smoke are just some of the issues that can be avoided by using a dry powder inhaler over a traditional cigarette. Dry powder inhalers allow users to inhale nicotine powder from an inhaler so that the aerosolized powder it is deposited on surfaces of the lungs and absorbed into the bloodstream. One such device has been described in U.S. Pat. No. 6,234,169 to Bulbrook et al. ("Bulbrook"), herein incorporated by reference in its entirety.

While there are numerous inhaler designs to effectively deliver dry powder compositions to the lungs, all such systems are designed to deliver an entire metered dose of powder medicament over a single inhalation. However, it may be desirable for users to inhale less than the entire metered dose of powder during each inhalation for a number of reasons. For instance, many dry powder inhaler users desire to mimic the experience of smoking a traditional cigarette. Unlike metered dose inhalers, when smoking a traditional cigarette, multiple drags or inhalations are taken from the cigarette before it is finished. Each drag gathers smoke filled with nicotine into the mouth, where it is subsequently inhaled so that the nicotine reaches the lungs for absorption into the bloodstream. Similarly, dry powder inhaler users may desire to take-in less than an entire metered dose with each inhalation so that the medicament is finished after multiple or variable number inhalations, similar to a traditional cigarette. Likewise, dry powder inhaler users may desire for the full nicotine dosage to hit their system in a more gradual fashion, over the course of multiple inhalations across a variable time period.

Another issue with conventional single inhalation devices is they are prone to under-dosage or over-dosage of powder due to user error. For instance, many inhalers require a specific inhalation technique that may me specific for that inhaler design. As one example, certain models of inhalers require the user to hold the device at a specific horizontal or tilted-angle orientation, for optimal dispensing into the upper respiratory system. Inhalation technique may also require users to undergo a specific breathing progression, such as a deep exhale of the lungs prior to a deep inhalation. If the user holds the inhaler at the wrong orientation, or fails to properly coordinate their breathing movement with dispensing of the powder, they may unintentionally cause the medicament to settle in areas of the mouth before reaching the upper respiratory system and lungs. At this point, the user is stuck trying to guess how much of the full dosage missed their upper respiratory tract, and whether or not they should take an additional dose to compensate for user error. Depending on what the user chooses to do, they run the risk of under-medicating, over-medicating or wasting powder.

Unfortunately, because dry powder inhalers cannot deliver a partial amount of the metered dosage with each inhalation, the desired physical maneuvers traditionally associated with smoking conventional cigarettes cannot be successfully mimicked. Further, because these devices cannot provide a mechanism for taking only a partial or variable amount of a full dosage, the impact of user error during any one particular partial dosage inhalation remains.

Thus, there is a need in the art for a device that is capable of delivering a partial or variable dosage of dry powder or medicament upon each single inhalation by the user, such that a user can effectively self-titrate the dose to a satiation level. Accordingly, the entire dose does not have to be inhaled unless desired by the user.

SUMMARY OF THE INVENTION

A dry powder inhaler is described. The inhaler includes a housing including a proximal end, a distal end and a chamber, wherein the housing further includes at least one opening in fluid communication with the chamber, and wherein the chamber includes at least one protrusion configured to limit the movement of a dry powder storage capsule when air flows through the chamber, such that only a portion of dry powder within the storage capsule is released into the flow of air for inhalation. In one embodiment, at least a portion of the chamber tapers down in a distal direction. In another embodiment, the chamber has a circular cross-section. In another embodiment, the protrusion is configured so that when the capsule is housed with within the chamber, a longitudinal axis of the capsule is skewed with a longitudinal axis of the chamber. In another embodiment, the at least one chamber opening is angled. In another embodiment, the movement is a spinning movement. In another embodiment, the movement is a sliding movement.

Another dry powder inhaler is also described. The inhaler includes a housing including a proximal end, a distal end, a dry powder chamber and an air chamber, wherein the air chamber includes a proximal opening and a distal end opening, a pressure actuated valve covering the distal opening, and a flapper element hinged to the housing and at least partially blocking a proximal portion of the air chamber, such that only a portion of dry powder within the dry powder chamber is released into the flow of air for inhalation. In one embodiment, the flapper element is configured to at least partially cover the air chamber in a first position responsive to a first pressure less than a threshold pressure. In another embodiment, the flapper element is configured to swing to a second position and at least partially cover an opening of the dry powder chamber responsive to a second pressure greater than the threshold pressure.

Another dry powder inhaler is also described. The inhaler includes a housing including a proximal end, a distal end, an air chamber, a dry powder chamber, an air inlet providing fluid communication between the dry powder chamber and an external environment, and a proximal end opening in fluid communication with the air chamber, wherein a distal opening portion of the housing includes a moving element configured to slide in a proximal and distal direction responsive to a pressure within the air chamber. In one embodiment, the moving element is configured to interface with a distal opening of the dry powder chamber and a distal opening of the air chamber responsive to a pressure within the air chamber.

Another dry powder inhaler is also described. The inhaler includes a housing including a proximal end, a distal end, an air chamber, a dry powder chamber, and a proximal end opening in fluid communication with the air chamber, wherein the dry powder chamber includes an opening in fluid communication with the air chamber, the opening sealed by a first pressure actuated valve configured to open responsive to a first threshold pressure.

A method of delivering an amount of a dry powder nicotine formulation in a variable number of inhalations is described. The method includes the steps of loading a full dose of a dry powder nicotine formulation into a chamber within a dry powder inhaler, inhaling through the inhaler mouthpiece, and inhibiting release of the full dose of dry powder nicotine during a first inhalation, such that at least two inhalations are required to take the full dose. In one embodiment, the dry powder formulation is contained in a capsule. In another embodiment, the step of inhibiting includes reducing movement of the capsule in the dry powder inhaler chamber. In another embodiment, the reduction of movement is actuated by a protrusion within the chamber. In another embodiment, the reduction of movement is actuated by a tapered region within the chamber. In another embodiment, the reduction of movement is actuated by a hinged panel. In another embodiment, the reduction of movement is actuated by friction via an applied force to a portion of the dry powder inhaler housing.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A shows the capsule and the airflow at the beginning of inhalation. FIG. 4B shows the capsule and the airflow as the capsule is drawn proximally in response to a negative pressure within the chamber. FIG. 4C shows the aerosolized powder traveling distally through the mouthpiece.

DETAILED DESCRIPTION OF THE INVENTION

Figure 1:
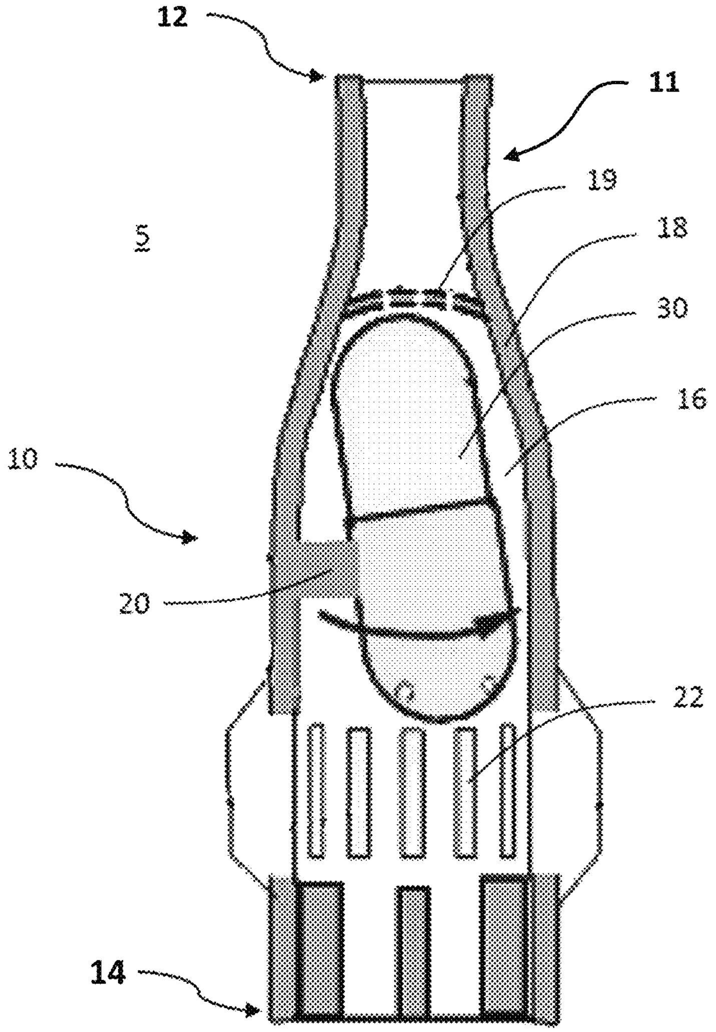
FIG. 1 is cross-sectional view of a dry powder inhaler with a protrusion limiting capsule spin according to an exemplary embodiment of the invention.

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a dry powder inhaler specifically designed for partial or variable dosage delivery per inhalation.

With reference to FIG. 1, a dry powder inhaler is shown according to an embodiment of the invention. The dry powder inhaler 10 includes a housing 18 having a proximal end 12 and a distal end 14. The proximal end 12 of the dry powder inhaler 10 features a circular opening as part of a mouthpiece component 11. The mouthpiece 11 can either be an attachable component, or molded as a single contiguous component with the rest of the dry powder inhaler housing 18. The housing 18 has a series of attached walls, or is molded as one contiguous wall that defines the outer surface contours of the dry powder inhaler 10. The housing 18 can also define the geometry of an air chamber 16 within the device and the mouthpiece 11. The air chamber 16 is in fluid communication with the mouthpiece 11, so that when a user inhales on the mouthpiece 11, a negative pressure or vacuum is created within the air chamber 16. A back stop or filter 19 has openings to permit flow of air between the air chamber 16 and the proximal end 12, and also prevents the capsule 30 from clogging the mouthpiece 11. Distal of the chamber 16 but proximal to the distal end 14 are angled air inlets 22 that facilitate the introduction of a "turbo spin" or "vortex" airflow effect within the air chamber 16. If the air inlets 22 are angled in substantially the same direction (e.g. clockwise or counterclockwise), as the user inhales on the mouthpiece 11, air is introduced into the air chamber 16 from the external environment 5. Airflow will travel from the external environment 5, through the air inlets 22, into the air chamber 16, out of the opening at the proximal end 12 and into the user's mouth. The decreasing cross-sectional area of the air chamber 16 in the proximal direction increases air pressure, leading to a burst of secondary airflow surrounding the capsule 30 and creating a vortex-like effect. This vortex airflow causes the capsule 30 to spin rapidly within the air chamber 16. Since the capsule is punctured, as it spins around in the air chamber 16, it dispenses powder into the primary airstream which is inhaled by the user. In certain embodiments, some of the air inlets are angled in one direction, while other are neutral and/or or angled in the opposite direction, for limiting the spin of the capsule during a single inhalation.

As illustrated in FIG. 1, the capsule 30 sits within the air chamber 16 at an angle. The angled stance of the capsule 30 is created by a protrusion 20 which is an internal component of the housing 18 that protrudes into the air chamber 16 cavity. As the vortex airflow acts to spin the capsule 30, the protrusion 20 has a limiting effect, limiting the duration of the spin by skewing the capsule 30 at an angle, slightly misaligned with the axis of the vortex and the longitudinal axis of the dry powder inhaler 10. In addition, the protrusion has a limiting effect by further interfering with the overall space that the capsule 30 has within the air chamber 16 to spin freely. Both of these limiting effects act to minimize and stop the spinning of the capsule 30, resulting in a partial dosage of powder dispensed during a single inhalation. The chase air provided by the air inlets 22 provides a smooth and full inhalation for the user by introducing air into the mouthpiece 11 from the external environment 5, even though air movement through the chamber 16 is restricted. Thus, dispensation of a full dosage of powder from the capsule requires multiple inhalations by the user. Shapes of protrusions disclosed herein are not limited to rectangular. Protrusion shapes may be any number of geometries, including but not limited to rounded, triangular, curved, straight, or any combination of these. Leaf springs, ribbed chambers, and non-circular chambers, such as a heart shaped or other concave and concave shaped chamber, can also be utilized to limit movement of the capsule. Further, more than one protrusion can be present, and multiple protrusions can have different shapes and heights. Multiple protrusions do not have to be spaced equidistant from each other. In certain embodiments, the protrusion is disposed within the device so that the capsule is likely to stop with the punctured portion of the capsule facing the mouthpiece. In other embodiments, the protrusion is disposed within the device so that the capsule is likely to stop with the punctured portion either perpendicular or facing away from the mouthpiece. Placement and design considerations of the protrusions can be based on the structure of the dry powder inhaler and the desired dosage of each inhalation.

Figure 2A:
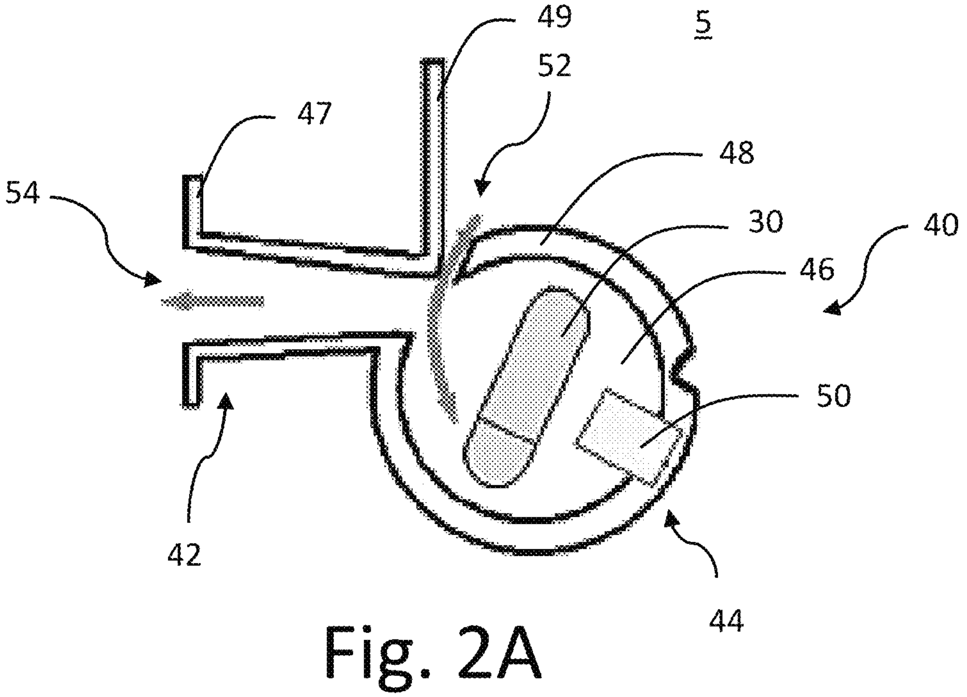
FIG. 2A is cross-sectional view of another dry powder inhaler with a protrusion limiting capsule spin according to an exemplary embodiment of the invention.
Figure 2B:
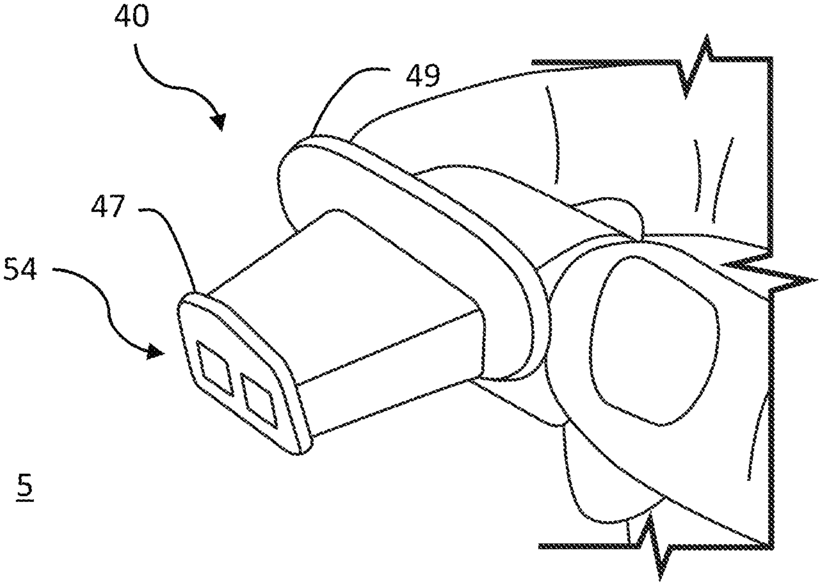
FIG. 2B is a perspective view of the dry powder inhaler of FIG. 2A.

Alternative embodiments of a dry powder inhaler with a protrusion for limiting capsule spin and administering a partial dosage of powder are shown in FIGS. 2A and 2B. With reference to the alternative embodiment shown in FIG. 2A, the dry powder inhaler 40 has a proximal end 42, a distal end 44, and a housing 48 defining a chamber 46 for the receipt of a dry powder capsule 30. Mouth guards 47, 49 are positioned on external surfaces of the dry powder inhaler 40 to allow for a better fit with the user's mouth during inhalation. One or more air inlets 52 are disposed adjacent to the mouthpiece 54 and the chamber 46. The air inlets 52 are positioned and angled for bringing air into the chamber 46 and mouthpiece 54 from the external environment 5, creating a circular airflow within the chamber 46 for spinning the capsule 30. As the punctured capsule 30 spins in the chamber 46, powder is dispensed in a primary airflow directed distally through the mouthpiece 54, entering the user's mouth during inhalation. A protrusion 50 is connected to or molded from the housing 48, and protrudes out into the cavity of the chamber 46. Without the protrusion 50, an unrestricted chamber may otherwise spin the capsule 30 such that the entire dosage of medicament is dispensed in a single inhalation. The protrusion 50 is configured to restrict the spin of the capsule 30 so that a single inhalation by the user yields only a partial dose of powder into the primary airflow. Not only does the protrusion 50 physically restrict movement of the capsule 30, it also interrupts the aerodynamic of the vortex, yielding a restricted movement of air within the chamber 46.

Figure 3A:
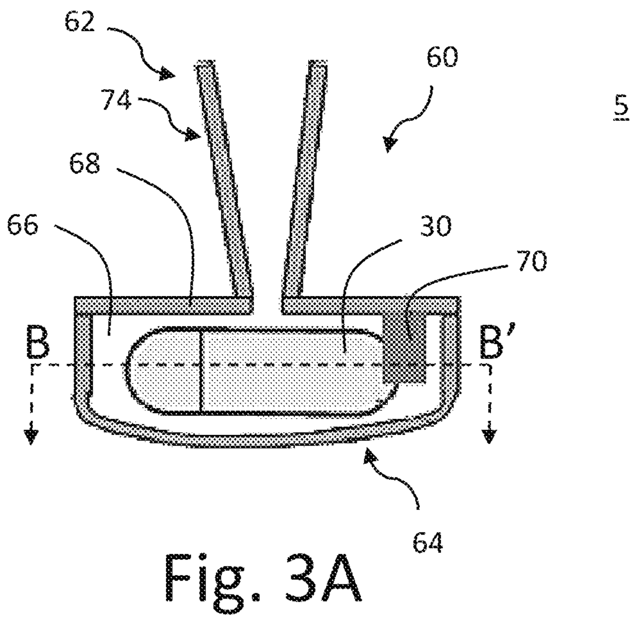
FIG. 3A is cross-sectional view of a dry powder inhaler with a protrusion limiting capsule spin according to an exemplary embodiment of the invention.
Figure 3B:
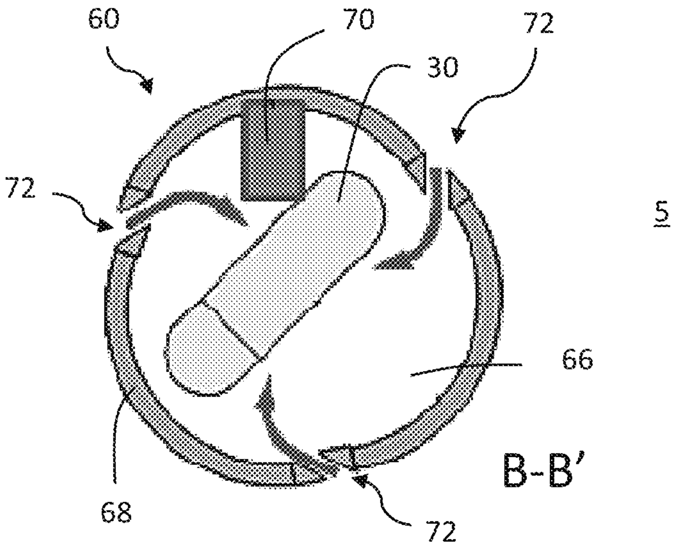
FIG. 3B is a cross-sectional view of the dry powder inhaler of FIG. 3A taken along cross-section B-B'.

Another alternative embodiment of a dry powder inhaler with a protrusion is shown in FIGS. 3A and 3B. The dry powder inhaler 60 has a housing 68 extending from a proximal end 62 to a distal end 64. The housing 68 defines the chamber 66 where the capsule 30 resides. The proximal end 62 of the inhaler 60 has a mouthpiece 74 for interface with the user's mouth. Air inlets 72 are disposed around the edges of the chamber 66 and penetrate the housing 68 at an angle so that as the user inhales on the mouthpiece 74, air is drawn from the external environment 5 to create a vortical airflow within the chamber 66. The vortical airflow spins the capsule 30 within the chamber 66, however, the protrusion 70 limits the duration of spin by limiting the space and range that the capsule is allowed to spin unrestricted. The protrusion 70 also interferes with the airflow dynamics within the chamber 66 so that a less than optimal vortex is created as the stream of air is partially blocked by the protrusion 70.

Figure 4A:
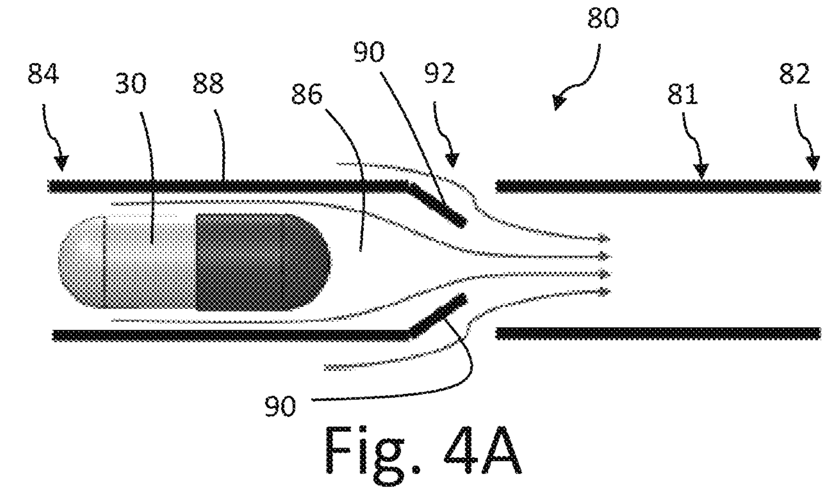
FIGS. 4A-4C are diagrams showing airflow within an exemplary dry powder inhaler housing having a sliding capsule mechanism according to an exemplary embodiment of the invention.
Figure 4B:
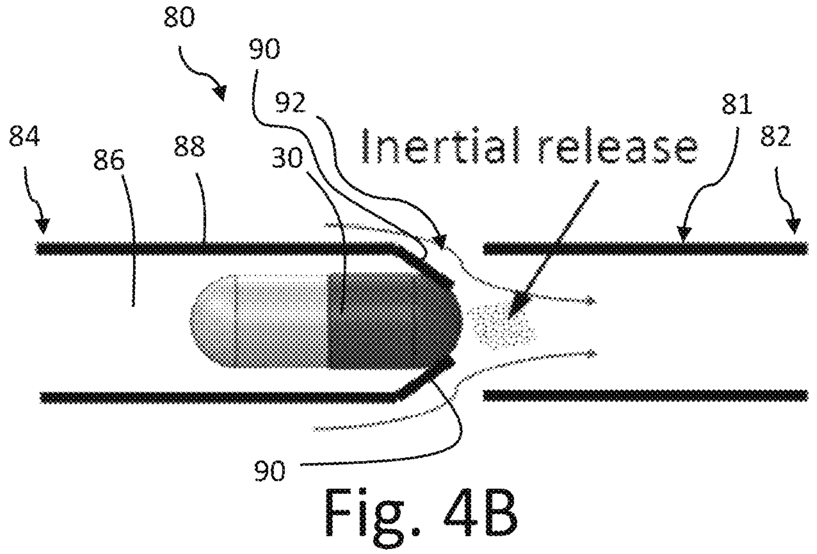
Figure 4C:
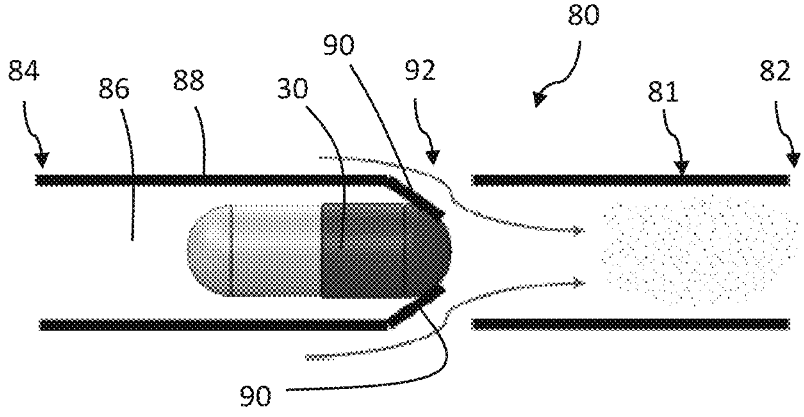
Figure 5A:
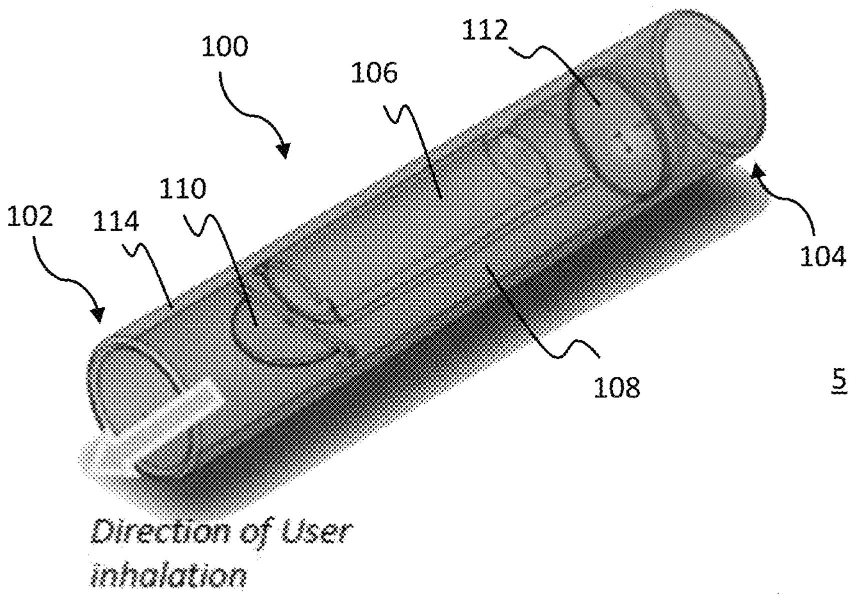
FIG. 5A is a perspective view of a dry powder inhaler with a hinged panel or flapper board mechanism according to an exemplary embodiment of the invention.
Figure 5B:
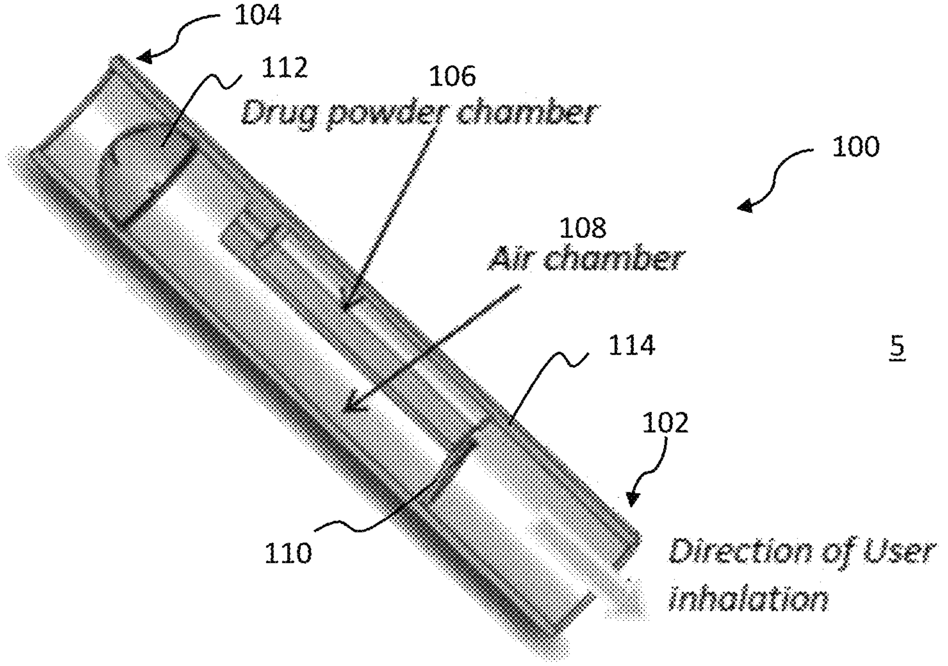
FIG. 5B is a cross-sectional view of the dry powder inhaler shown in FIG. 5A.
Figure 5C:
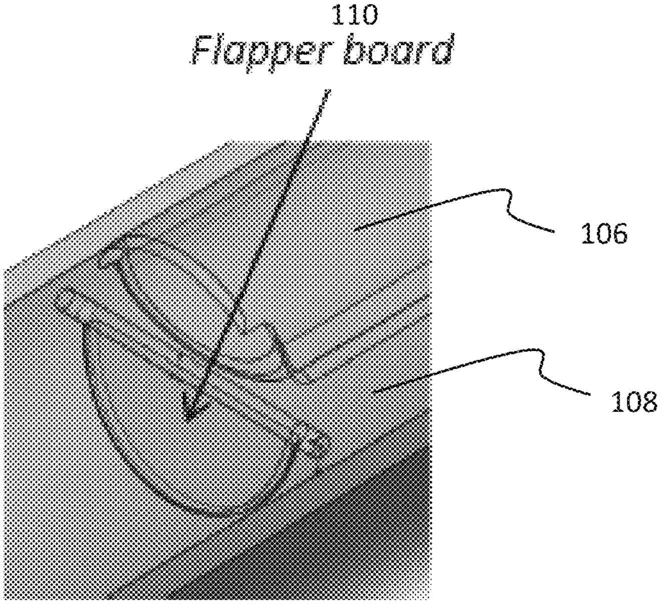
FIG. 5C is a magnified view of the panel in a down position and the drug chamber is open.
Figure 5D:
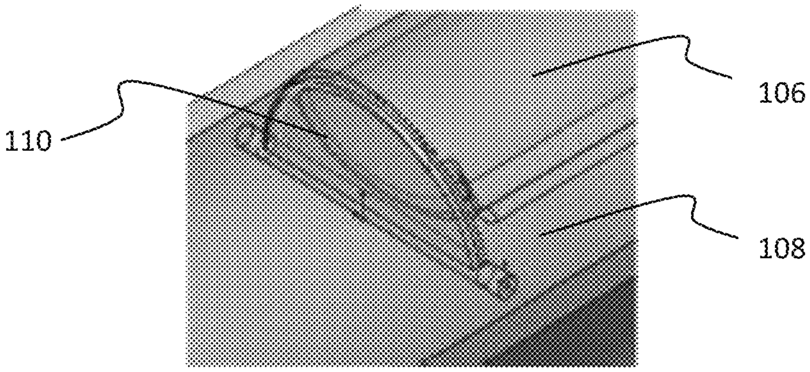
FIG. 5D is a magnified view of the flapper board up position and the drug chamber is closed.

In certain embodiments, powder from the pierced capsule is dispensed into the mouthpiece through a sliding motion of the capsule, rather than a spinning motion of the capsule. With reference to FIGS. 4A-4C, a dry powder inhaler 80 has a housing 88 extending between a distal end 84 and a proximal end 82 of the device, with a mouthpiece 81 situated at the proximal end 82 for user inhalation. As shown in FIG. 4A, as the user inhales on the mouthpiece 81, a negative pressure builds up internally within the housing 88, moving air through the chamber 86 and the mouthpiece 81 in a proximal direction. As the negative pressure within the housing 88 rapidly builds, the capsule 30 starts to slide and accelerate in the proximal direction with the direction of flow of air. Protrusions 90 extending into interior cavities of the housing 88 create a portion of the chamber 86 that is less than the diameter of the proximally punctured capsule 30. As illustrated in FIG. 4B, the protrusions 90 stop the proximal sliding movement of the capsule 30. This interface creates a check valve as the capsule 30 strikes the protrusions 90 on the distal end of the chamber 86 for initiating a partial dosage ejection of powder my means of an inertial release. As in previous embodiments and as shown in FIG. 4C, a continued chase flow of chase air flows through air inlets 92 continue even after the chamber 86 is plugged by the capsule 30, and the capsule 30 has stopped moving within the chamber 86 during the inertial release of powder. The chase air flow helps to aerosolize the powder, while providing the user with a smooth and full finish to their inhalation. In certain embodiments, the air inlets 92 are angled so that a vortical airflow is introduced into the cavities of the housing.

Dry powder inhalers according to this and other embodiments disclosed herein can be manufactured with advantages that cause users to mimic maneuvers associated with smoking a conventional cigarette. For instance, in the embodiment shown in FIGS. 4A-4C, as the user inhales, the capsule is rapidly accelerated proximally into the tapered protrusion geometry of the distal portion of the chamber. If the angle of the taper is shallow enough, the capsule can become temporarily stuck and lodged between tapered walls so that the user has to tap or jolt the inhaler in order to reset the capsule to the distal end of the inhaler. This action may be preferential for some users who desire to mimic the traditional maneuver of "flicking off the ashes" on a conventional cigarette. As a conventional cigarette burns, the part that has already been smoked remains at the distal tip in the form of a fine gray ash. Often, the ash will not fall from the cigarette unless a flicking motion (e.g. tapping and end of the cigarette with one or more fingers) is executed to jolt the ash loose. Thus, designs that manage to sandwich the sliding capsule within the tapered region, requiring a jolt to loosen it again, may incorporate maneuvers that coincide with smoking a traditional cigarette. In addition, "stubbing out" a cigarette, which is essentially a maneuver for grinding the end of a cigarette against a surface for safe disposal after you are finished with it, is another maneuver that could be mimicked for jolting the capsule loose.

Now with reference to FIGS. 5A-5D, embodiments of the invention utilize a swinging flapper board for providing a partial dosage per inhalation. The dry powder inhaler 100 has a housing 114 extending between a proximal 102 end and a distal end 104. The exterior profile of the housing 114 is substantially cylindrical, with circular openings at either end of the inhaler 100. A portion of the housing 114 further defines an upper chamber serving as the drug powder chamber 106, and a lower chamber serving as an air chamber 108, both within the housing 114. The drug powder chamber 106 is designed to contain the dry powder medicament, while the lower air chamber 108 is designed to provide an airflow pathway between the user's mouth, the drug powder chamber 106 and the external environment 5. The two chambers 106, 108 overlap in a mid-section of the inhaler 100. A flapper board 110 is connected to internal portions of the housing 114 using a hinged connection. As shown with more detail in the magnified views of FIGS. 5C and 5D, the flapper board 110 is shaped to both swing freely within the cavity of the housing 114, and to cover the proximal opening of the drug powder chamber 106 when swung upright. With reference back to FIGS. 5A and 5B, the distal end of the housing 114 features a check valve 112, opening when a threshold pressure is reached within the air chamber 108. The flapper board 110 can be made of any suitable material known in the art, including elastomers such as silicone and certain medical grade plastics, and is substantially semicircular or D-shaped. The check valve 112 can be made of materials known in the art such as elastomeric silicone. In this embodiment and in other embodiments described herein, the check valve 112 is dome shaped with a plurality of intersecting slits that upon responsive to a threshold pressure. In alternative embodiments, the check valve can be a disc valve, a duckbill valve, or other valve configurations known in the art. Elastomeric check valves can have one slit, or a plurality of intersecting or nonintersecting slits.

As shown in FIGS. 5A-5D, the flapper board 110 is near the opening at the proximal end 102 of the inhaler 100 and the check valve 112 is at the opposite distal end 104 of the inhaler 100. As the user starts to inhale on the proximal end 102 and create a negative pressure within the housing 114, they will inhale a small amount of powder from the drug powder chamber 106. As shown with more detail in FIG. 5C, the flapper board 110 is initially down just as the user begins to inhale. As the user's inhale reaches a certain threshold pressure level, the check valve 112 will open responsive to reaching the threshold, causing the flapper board to flip upright as air from the external environment 5 is introduced into the air chamber 108. As shown with more detail in FIG. 5D, the flapper board 110 closes the drug chamber 106 when in the upright position. As a result, chase air from the external environment 5 enters the primary air stream via the air chamber 108, and the user can complete their inhale. During a single inhalation, the user has picked-up only a partial amount of the powder stored in the drug powder chamber 106.

Figure 6A:
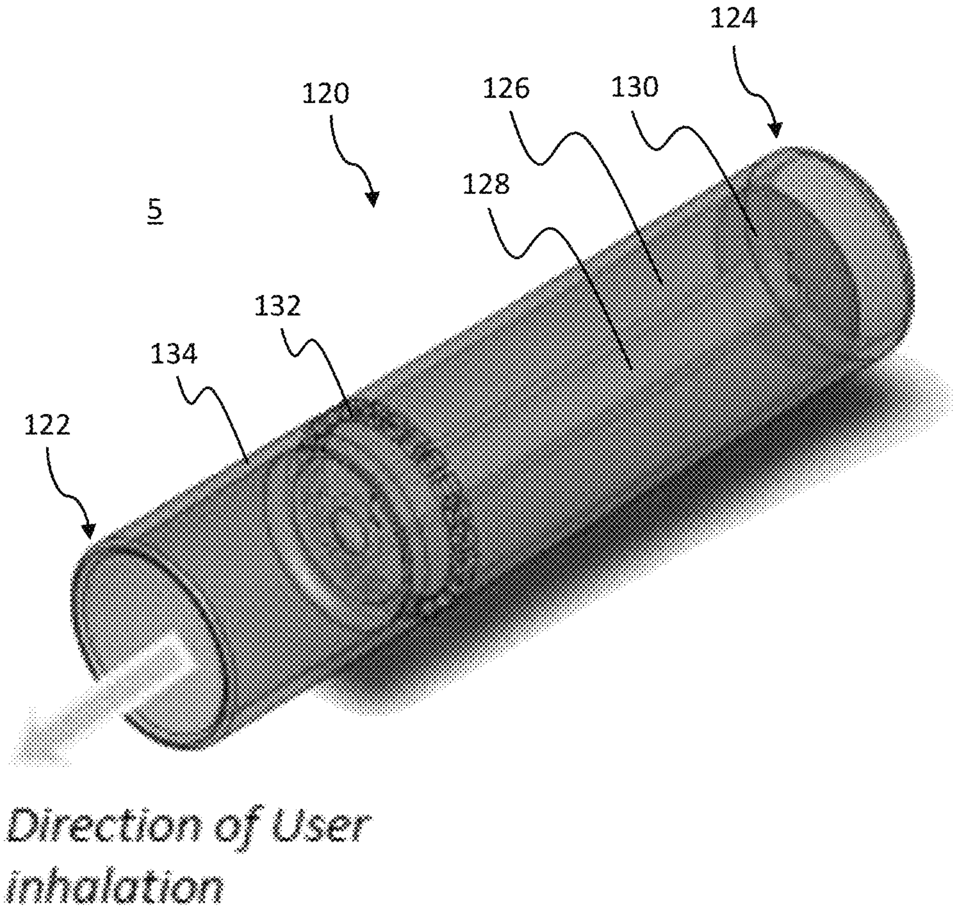
FIG. 6A is a perspective view of a dry powder inhaler with a moving board mechanism according to an exemplary embodiment of the invention.
Figure 6B:
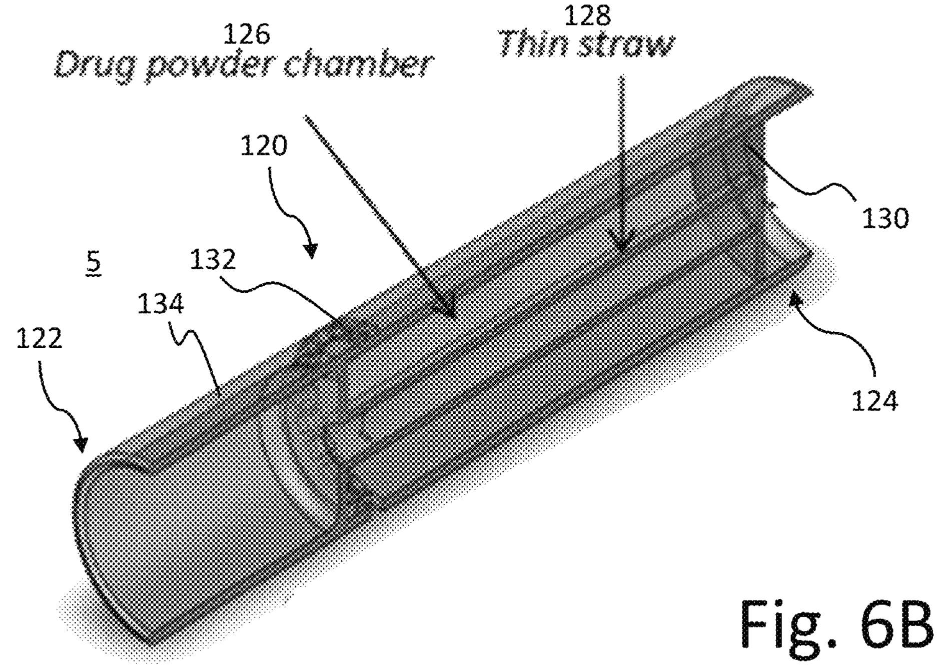
FIG. 6B is a cutaway perspective view of the dry powder inhaler shown in FIG. 6A.
Figure 6C:
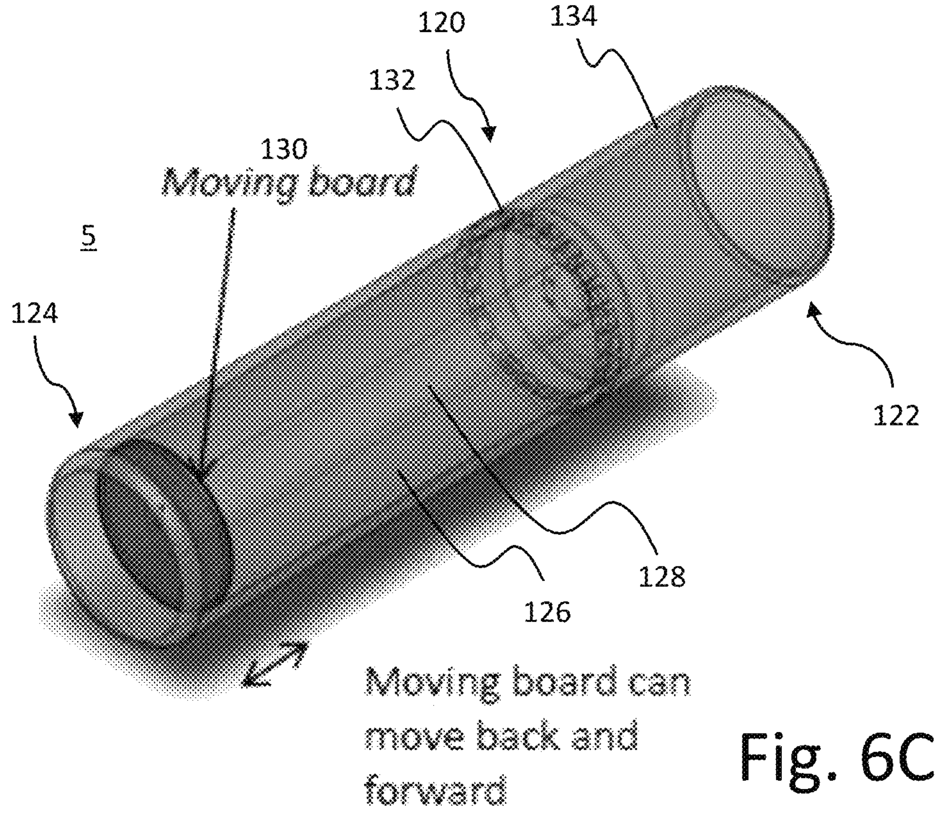
FIG. 6C is an alternate perspective view of the dry powder inhaler shown in FIG. 6A.
Figure 7A:
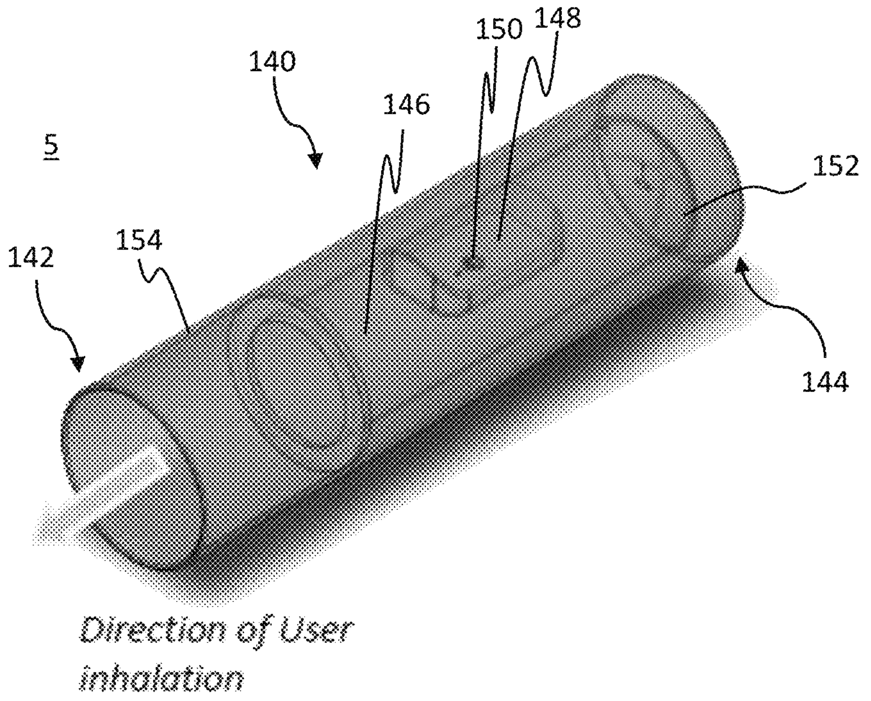
FIG. 7A is a perspective view of a dry powder inhaler having a drug powder chamber with a check valve according to an exemplary embodiment of the invention.
Figure 7B:
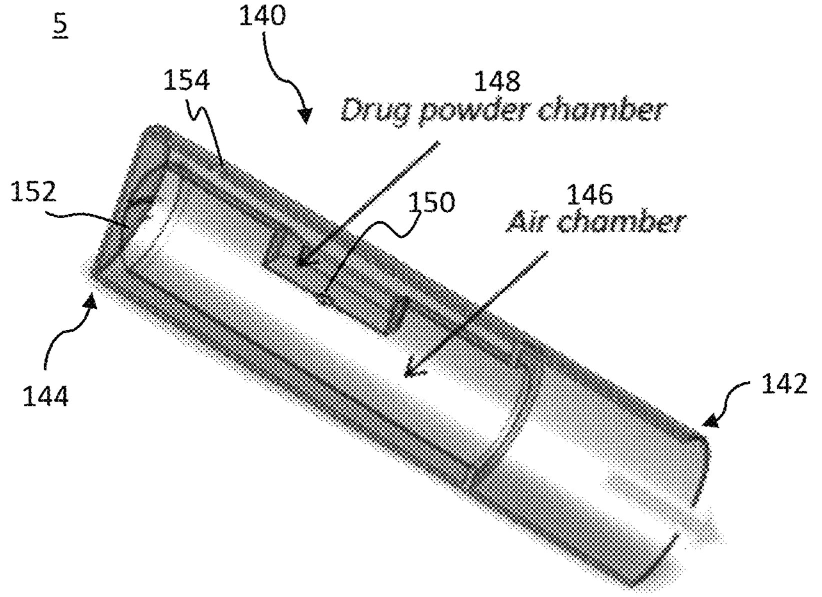
FIG. 7B is a partial cutaway perspective view of the drug powder inhaler shown in FIG. 7A.
Figure 7C:
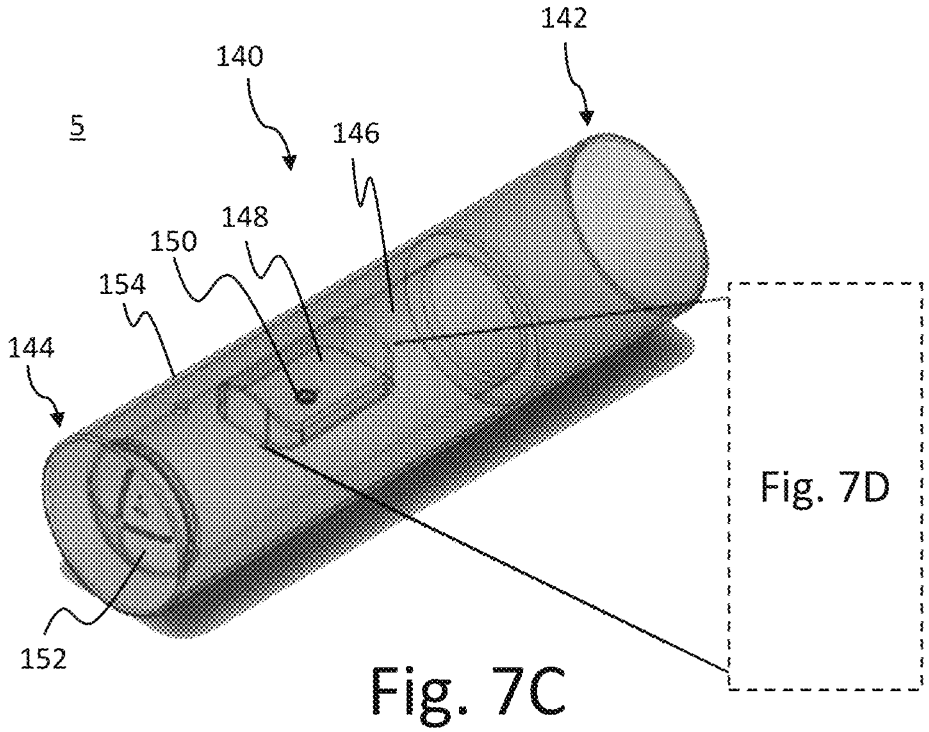
FIG. 7C is an alternative perspective view of the drug powder inhaler shown in FIG. 7A.
Figure 7D:
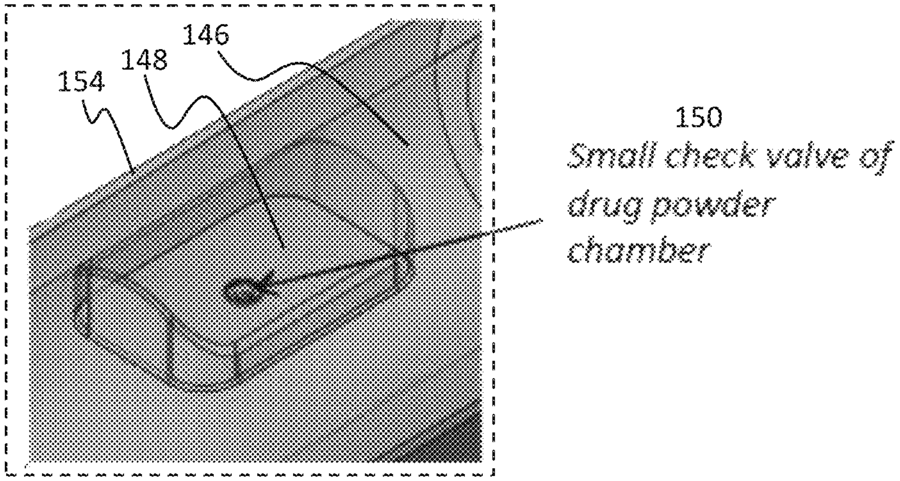
FIG. 7D is a magnified view of the drug powder chamber housed in the dry powder inhaler shown in FIG. 7A.

An alternative embodiment for providing a user with a partial dosage of powder in a single inhalation is shown in the dry powder inhaler of FIGS. 6A-6C. The dry powder inhaler 120 has a proximal end 122, a distal end 124 and a cylinder shaped housing 134 extending therebetween. A portion of the housing 134 forms a thin straw 128 running longitudinally through the center of the inhaler 120. Coaxially surrounding the thin straw 128 is the drug powder chamber 126 for storing powder medicament. Air inlets 132 are positioned in fluid communication with the drug powder chamber 126 for allowing the inflow of air from the external environment 5 into cavities of the housing 134. A moving board 130 is positioned within the distal end 124 of the housing 134. The moving board 130 is essentially a circular disk having a diameter slightly smaller than the diameter of the housing 134 cavity at the distal end 124. The moving board 130 has a thickness or height that keeps the disk shaped element flush against internal housing 134 walls so that it does not flip or twist. As shown in FIG. 6C, the moving board 130 can slide proximally or distally along the longitudinal axis of the inhaler 120. A lip structure of the distal end 124 of the housing 134 prevents the moving board 130 from sliding distally out of the housing 134.

During operation, a user generates a negative pressure at the proximal end 122 of the inhaler 120 during inhalation. The moving board 130, which is normally free to slide back and forth at the distal end 124 of the inhaler 120, will accelerate proximally with the direction of airflow and eventually interface with distal end 124 openings of the drug powder chamber 126 and the thin straw 128. Since the moving board 130 is sized to fill the diameter of the cavity at the distal end 124 of the housing 134, the board 130 effectively plugs the air pathways of the drug powder chamber 126 and the thin straw 128. Nonetheless, the user can continue to inhale a partial dose of powder since a small amount of powder has been introduced into the primary airflow and the thin straw 128 prior to the plugging of the air pathways by the moving board 130. As the inhalation pressure enters a peak, the powder is aerosolized, and subsequently enters the user's upper respiratory tract and lungs. As the user completes the inhalation, the moving board becomes loose again and a small amount of powder will again fall into the thin straw 128, ready for the next inhalation. Normally, gravity and inhalation forces will be adequate for knocking small amounts of powder into the primary airflow and the thin straw. Maneuvers such as "flicking off the ashes" or "stubbing out" as described above can also be used to knock small amounts of powder into the thin straw between inhalations.

Now with reference to FIGS. 7A-7D, an alternate embodiment of a dry powder inhaler having a small check valve on the dry powder chamber and a second check valve running across the air chamber is shown. The dry powder inhaler 140 has a proximal end 142, a distal end 144 and a housing 154 extending therebetween. The outer surface of the housing 154 has a substantially cylindrical shape. The user inhales through the proximal end 142 of the inhaler, generating a negative pressure within the air chamber 146. The air chamber 146 is adjacent the drug powder chamber 148, which serves as reservoir for storing a bulk amount of powder medicament. A small check valve 150 seals an opening in the drug powder chamber 148, so that powder cannot pass into the air chamber 146 unless the small check valve 150 actuates open. The small check valve 150 can be an elastomeric pressure actuated valve known in the art or described herein, such as a silicone slit valve. The small check valve 150 is configured to actuate open in response to a negative pressure within the air chamber 146. The air chamber 146 extends from the distal end 144 opening of the housing 154 to the proximal end 142 opening. A larger check valve 152 lies across the distal end 144 opening of the housing, and is configured to actuate in response to a second threshold pressure. The second threshold pressure required to actuate the larger check valve 152 is greater than the first threshold pressure required to actuate the smaller check valve 150.

As the user starts to inhale on the proximal end 142 opening of the inhaler 140, a negative pressure is generated in the air chamber 146. Since the threshold resistance of the small check valve 150 is less than the threshold resistance of the larger check valve 152, the small check valve 150 will open first as negative pressure builds, and a partial amount of drug powder will fall into the air chamber for the user to inhale. As negative pressure within the air chamber 146 becomes higher, the larger check valve 152 will open, which substantially reduces the negative pressure in air chamber 146 and causes the small check valve 150 to close to keep more drug powder from falling. Dry powder inhalers 140 according to this design can dispense a partial dose of powder over a single inhale, while allowing for a smooth inhalation of chase air for comfortably sending the aerosolized powder into the upper respiratory tract and into the lungs.

Figure 8A:
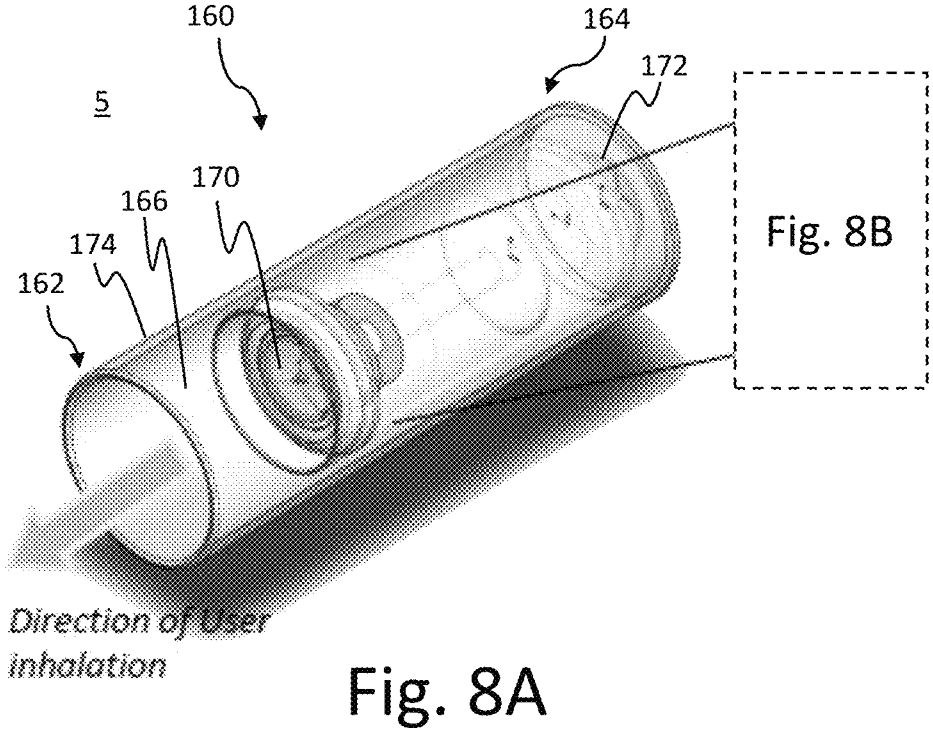
FIG. 8A is a perspective view of a dry powder inhaler with a sliding block mechanism according to an exemplary embodiment of the invention.
Figure 8B:
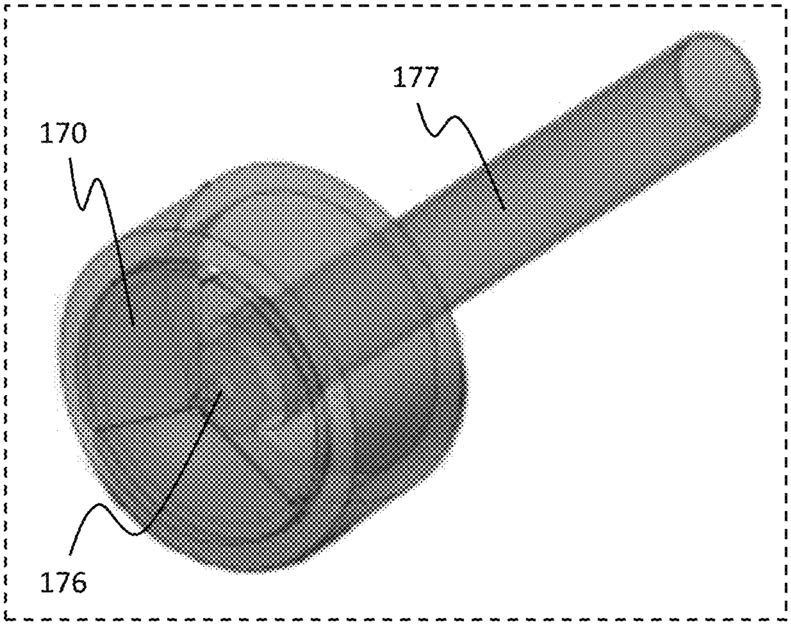
FIG. 8B is a magnified view of a check valve region shown in the dry powder inhaler of FIG. 8A.
Figure 8C:
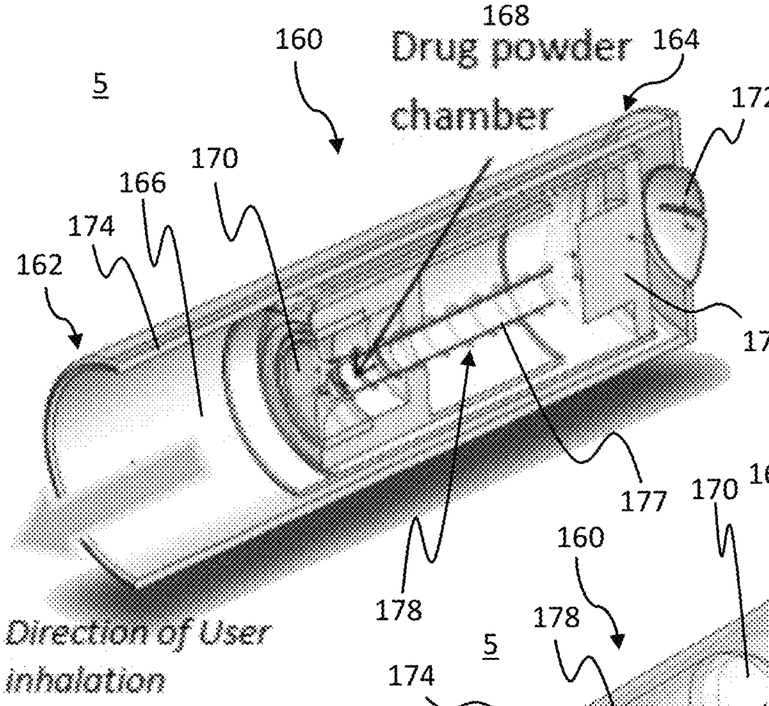
FIG. 8C is a cutaway perspective view of the dry powder shown in FIG. 8A.
Figure 8D:
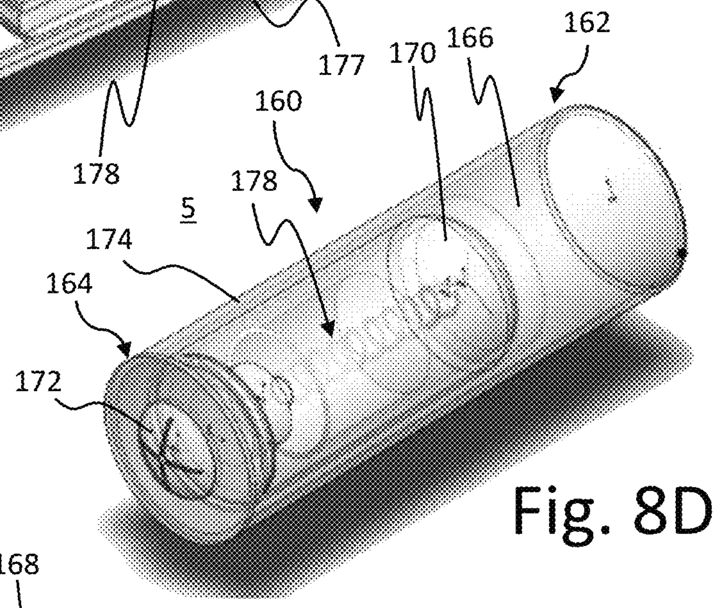
FIG. 8D is an alternate perspective view of the dry powder inhaler shown in FIG. 8A.
Figure 8E:
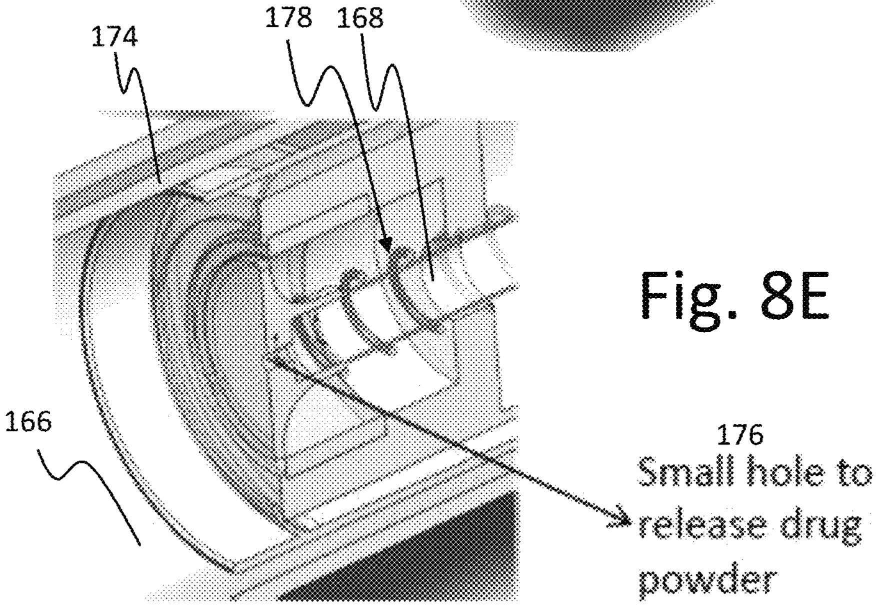
FIG. 8E is a magnified view of the drug release opening in the dry powder inhaler shown in FIG. 8A.

Certain embodiments of the invention use a spring mechanism for dispensing a partial amount of powder into the inhalation primary airflow, as shown in FIGS. 8A-8E. The dry powder inhaler 160 has a proximal end 162 and a distal end 164 with a housing 174 extending therebetween. The housing 174 holds an air chamber 166 and a drug powder chamber 168 (see FIGS. 8C and 8E) for holding dry powder such as nicotine powder. A first check valve 170 is fixed to the proximal end 162 of the drug powder chamber 168 and a block 179 is fixed to the distal end 162 of the drug powder chamber 168. A second check valve 172 is fixed to the distal end of the air chamber 166. As shown in FIG. 8B, the first check valve 170 has three slits that meet at the center of the elastomeric valve member. With reference to FIG. 8C, a spring 178 wrapped around a column 177 applies a small compression force to the block 179, biasing the block 179 towards the distal end 164 of the housing 174. If the block 179 is moved in a proximal direction, the first check valve 170 slits will crack the valve open. As shown in the magnified view of FIG. 8E, a small hole 176 centered at the proximal end of the drug powder chamber 168 is also aligned with the center of the first check valve 170. This small hole 176 is configured to dispense partial dosages of powder as the block 179 moves proximally, shifting powder proximally and pushing it through the small hole 176 and the slits in the first check valve 170. As the user begins to inhale from the proximal end 162 of the air chamber 166, a negative pressure begins to build in cavities of the air chamber 166. This pressure extends from the proximal end 162 opening to the second check valve 172 at the distal end 164 of the housing 174. When the negative pressure reaches a threshold level, the second check valve 172 will open, allowing additional air to enter the air chamber from the external environment 5. Incoming air moving proximally through the housing 174 will push the block 179 against the spring 178 column 177, shifting powder proximally and pushing a partial dosage of powder through the small hole 176 as the first check valve 170 cracks open. The primary airflow aerosolizes the powder for inhalation by the user. The remaining powder is secured within the reservoir until the next inhalation by the user.

Figure 9A:
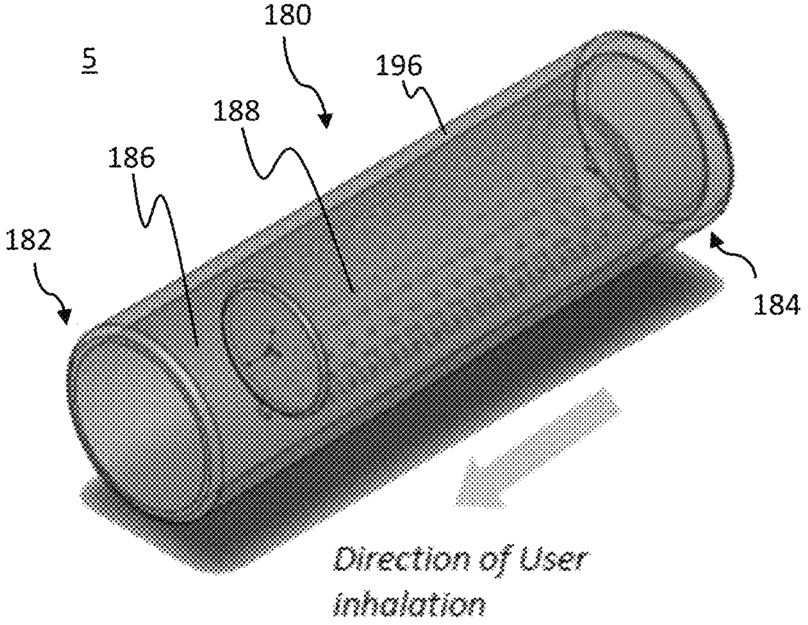
FIG. 9A is a perspective view of a dry powder inhaler with dry powder reservoir having a pattern of small holes according to an exemplary embodiment of the invention.
Figure 9B:
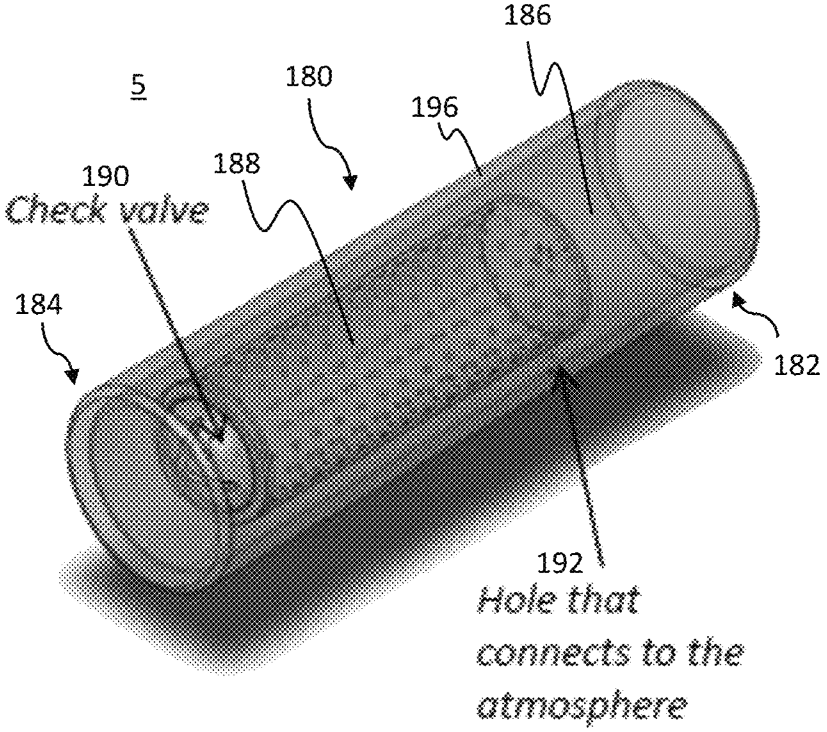
FIG. 9B is an alternate perspective view of the dry powder inhaler shown in FIG. 9A.
Figure 9C:
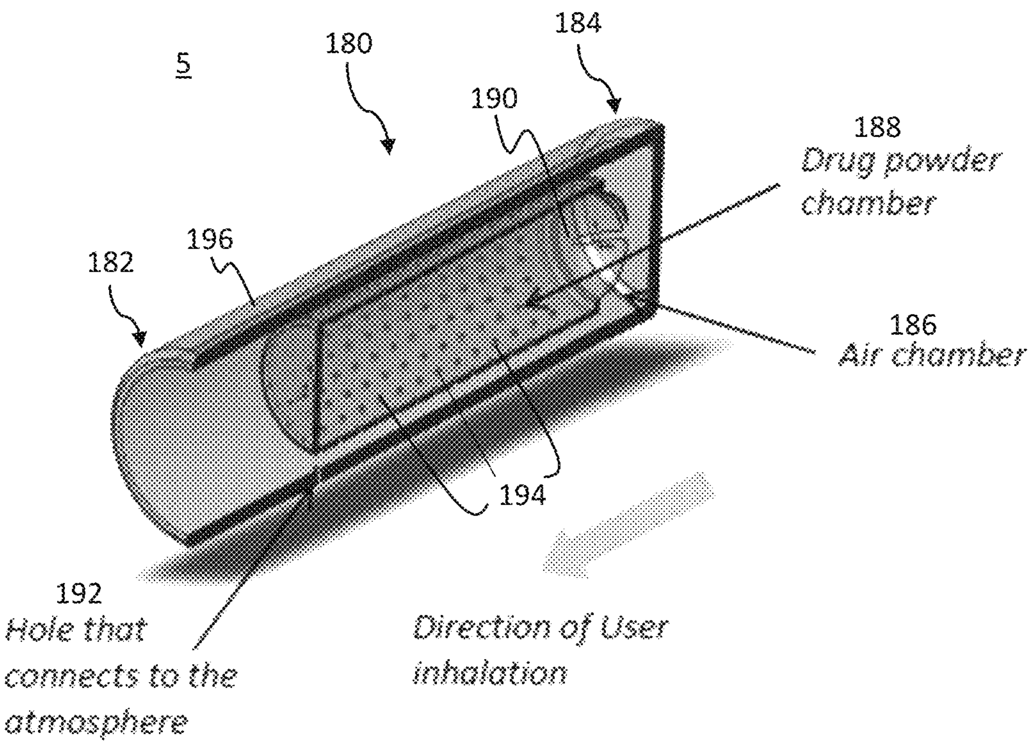
FIG. 9C is a cutaway perspective view of the dry powder inhaler shown in FIG. 9A.

Another exemplary embodiment of the invention utilized a dry powder reservoir having a grid of tiny openings for dispensing powder into an air chamber, as shown in FIGS. 9A-9C. The dry powder inhaler 180 has a housing 196 extending between a proximal 182 and distal 184 end. The interior of the housing 196 includes an air chamber 186 extending the length of the inhaler 180. The distal end 184 of the air chamber 186 is capped, while the proximal end 182 of the air chamber 196 is open. A hole 192 in the side of the housing 196 equalizes the pressure in the air chamber 186 with the atmospheric pressure of the external environment 5. The interior also houses a cylindrical dry powder chamber 188 featuring a pattern of holes 194 that are in fluid communication with the air chamber 186, shown with detail in FIG. 9C. The holes 194 permit very small amounts of powder to pass through to the air chamber 186. In certain embodiments, the holes 194 are slightly larger than the size of a single powder particle. In other embodiments, the holes 194 range in diameters of 2-5 times the size of a single powder particle. The hole 194 diameters can vary in size, and in certain embodiments, gradually change diameters moving in a proximal direction. The distal end of the dry powder chamber 188 features a pressure actuated check valve 190. When the user initiates inhalation on the proximal end 182 of the housing 196, negative pressure is generated within the air chamber 186. The airflow generated by the negative pressure causes powder to squeeze through the holes 194 in the dry powder chamber 188. Transfer of the dry powder from the dry powder chamber 188 to the air chamber 186 is facilitated by the check valve 190 that opens in response to a threshold pressure. The check valve 190 permits an inside-out airflow inside the dry powder chamber 188, pulling air in from the air chamber 186 and forcing powder back out into the primary airflow of the air chamber 186. Partial dosages of powder aerosolize in the primary airflow for inhalation by the user. The hole 192 in the side of the housing 196 connects the air chamber 186 to the atmosphere 5 so that it will balance the pressure slowly to stop the drug powder from falling down all the time.

Figure 10A:
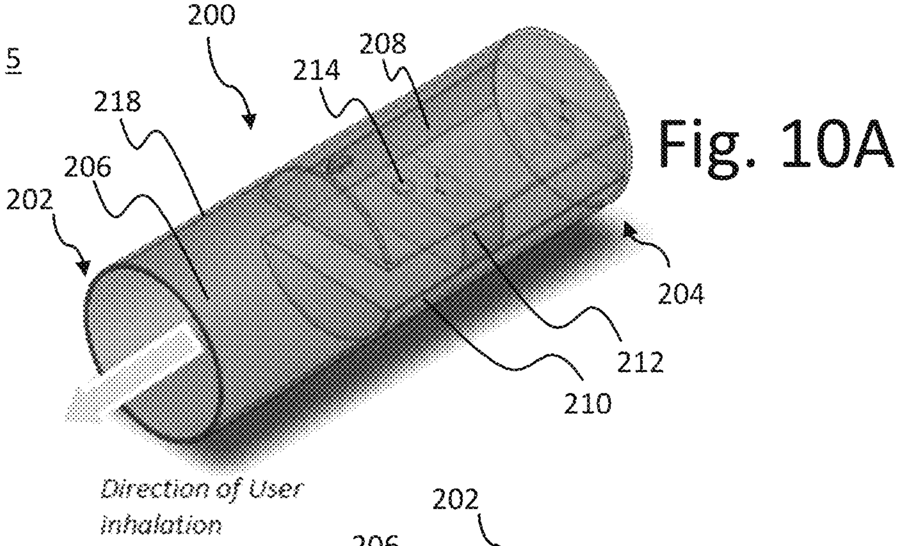
FIG. 10A is a perspective view of a dry powder inhaler with a sliding block mechanism according to an exemplary embodiment of the invention.
Figure 10B:
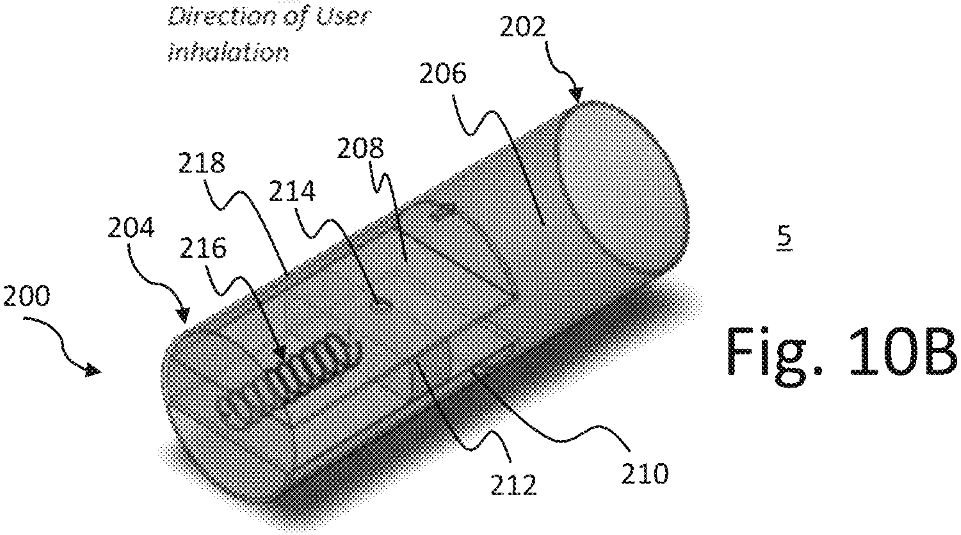
FIG. 10B is an alternative perspective view of the dry powder inhaler shown in FIG. 10A.
Figure 10C:
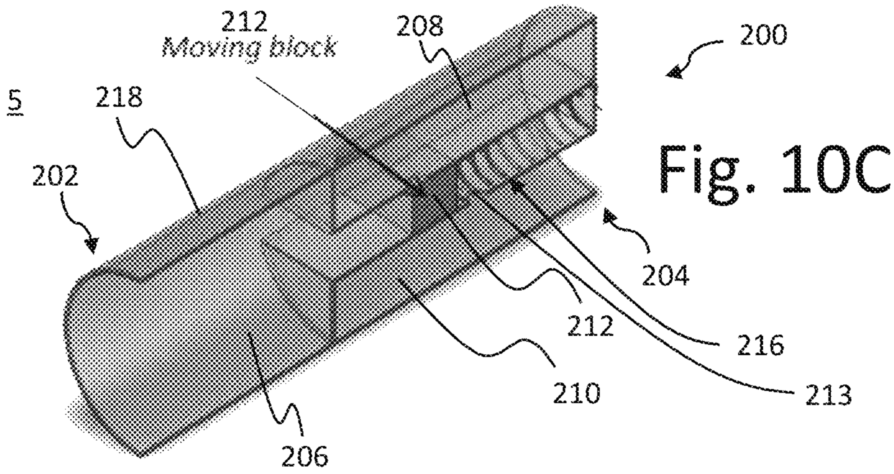
FIG. 10C is a cutaway perspective view of the dry powder inhaler shown in FIG. 10A.
Figure 11A:
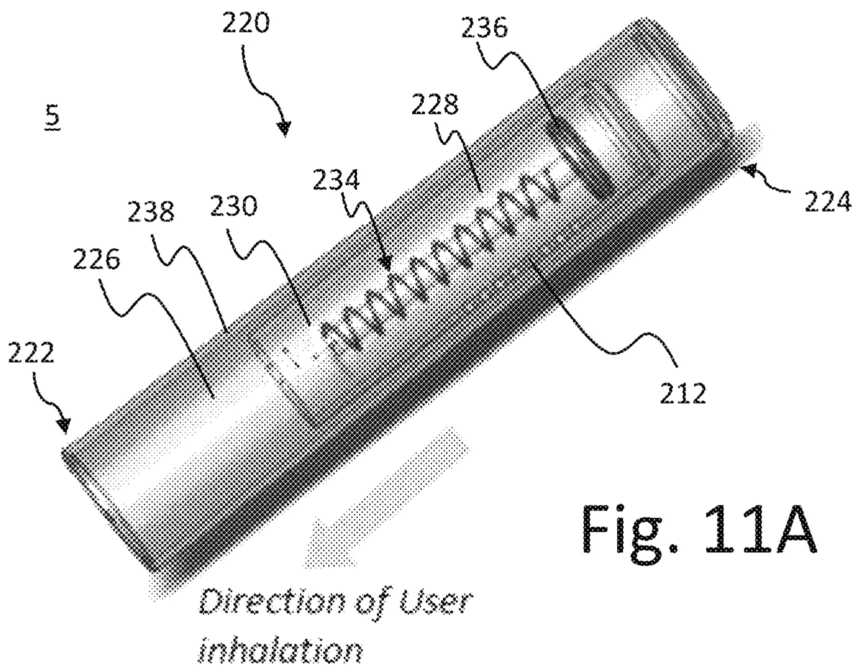
FIG. 11A is a perspective view of a dry powder inhaler with a moving board mechanism according to an exemplary embodiment of the invention.
Figure 11B:
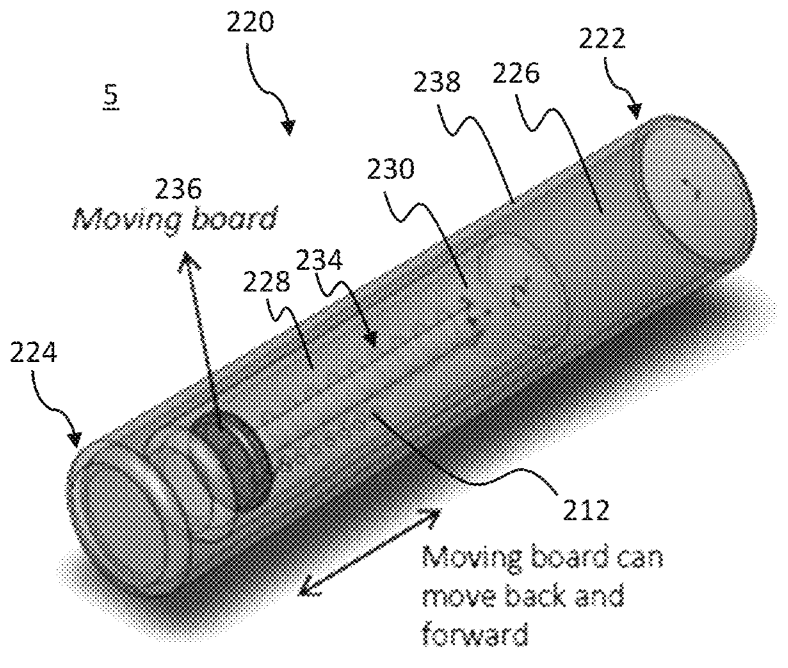
FIG. 11B is an alternate perspective view of the dry powder inhaler shown in FIG. 11A.
Figure 11C:
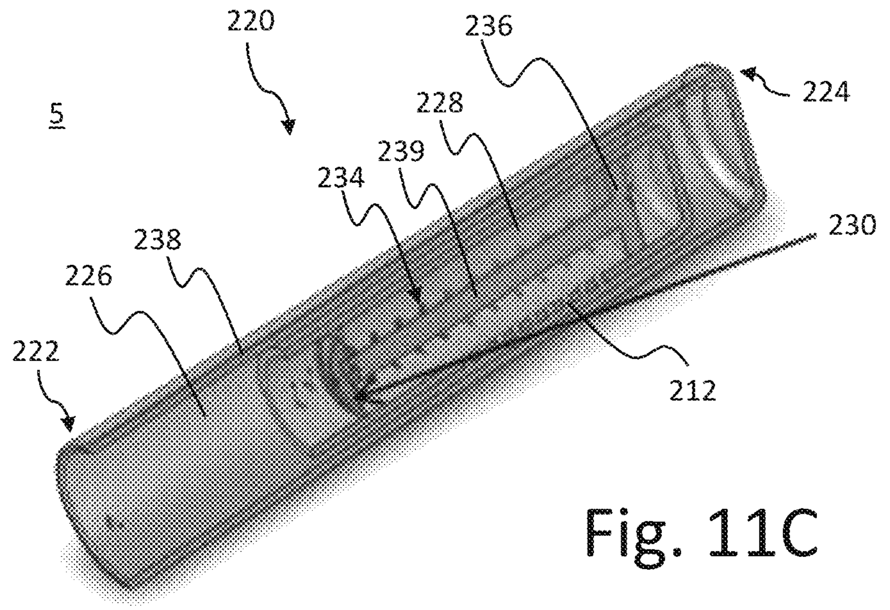
FIGS. 11C and 11D are cutaway perspective views of the dry powder inhaler shown in FIG. 11A.
Figure 11D:
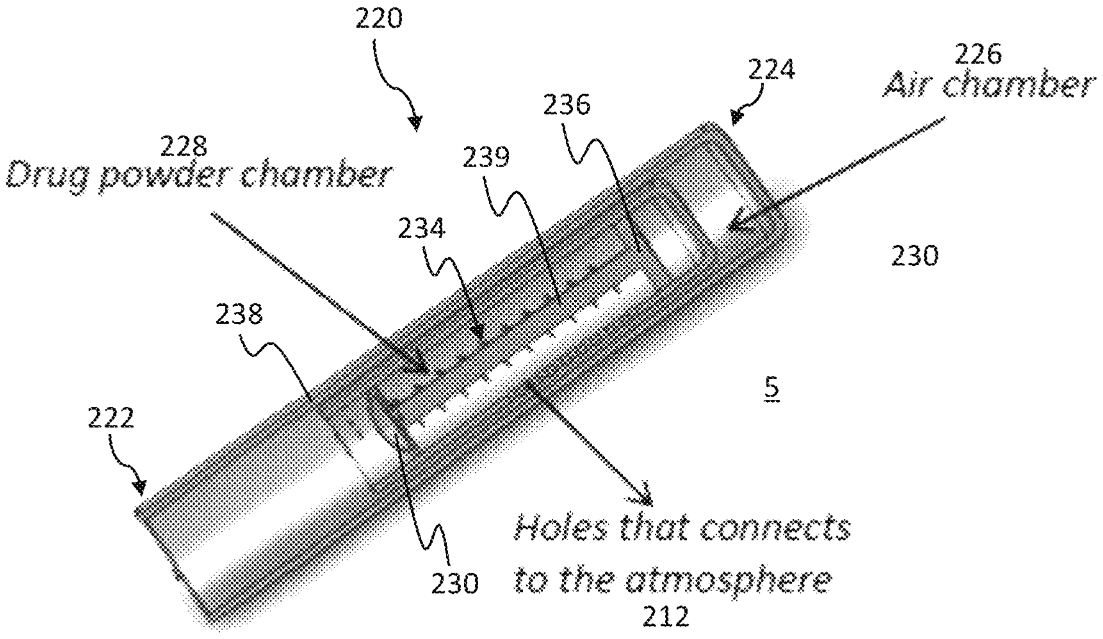

Another embodiment of a dry powder inhaler utilizing a spring and a moving block is shown in the dry powder inhaler of FIGS. 10A-10C. The dry powder inhaler 200 has a cylindrical housing 218 extending from a proximal end 202 to a distal end 204. The distal end 204 of the housing 218 includes an air chamber 206 in fluid communication with the opening on the proximal end 202 of the housing 218, and two opposing D-shaped chambers. The top D-shaped chamber is the dry powder chamber 208, which stores bulk amounts of powder medicament. The proximal and distal ends of the dry powder chamber 208 are capped, and the bottom floor of the dry powder chamber has a small opening 214 that allows powder small amounts of powder to fall from the dry powder chamber 208 into the air chamber 206. In certain embodiments, the small opening 214 is sealed by a check valve that opens in response to a negative pressure within the air chamber initiated by the start of user inhalation. The bottom chamber is the external air chamber 210, which is capped at its proximal end and open at its distal end in fluid communication with the external environment 5. As shown in FIG. 10C, the top of the external air chamber has an air opening 213 to allow air into the air chamber 206. In alternative embodiments, the air opening 213 is in the proximal cap of the external air chamber, optionally sealed with a check valve to open for chase air as the user inhaled powder medicament. With reference now to FIGS. 10B and 10C, a spring 216 is attached to the back of a block 212 that slides along the bottom surface of the dry powder chamber 208 and the top surface of the external air chamber 210. The block is biased towards a distal end of the air chamber 206 by the spring 216, which is connected to a capped distal end of the air chamber 206. During operation, the user inhales through the proximal end opening of the housing 218, generating a negative pressure within the air chamber 206. Since the block 212 starts off in a relaxed state at the distal end of the air chamber 206, biased distally by the spring 216, the opening 214 to the dry powder chamber 208 is uncovered, and a small amount of powder is present in the air chamber 206. As the user ramps up their inhale, air from the external environment 5 is introduced into the external air chamber 210 and drawn into the main air chamber 206 through the air opening 213. This creates a proximally directed primary airflow towards the user's mouth. The negative pressure will eventually reach a threshold which slides the block 212 far enough proximally so that the block 212 covers the small opening 214 in the dry powder chamber 208, ensuring that no more dry powder leaves the dry powder chamber 208 during that inhalation. As the user approaches the peak of their inhalation, the primary airflow aerosolizes the powder present in the air chamber 206 so that it enters the upper respiratory tract and lungs of the user. As the user winds down their inhalation, the block 212 slides back distally towards its original biased position, and a small amount of powder drops back into the air chamber 206, ready for next inhalation.

A moving board embodiment of a dry powder inhaler is shown in FIGS. 11A-11D. The dry powder inhaler 220 has an air chamber 226 extending between a proximal end 222 and a distal end 224 of the device. The dry powder chamber 228 stores bulk powder medicament and has a moving board 236 at its distal end and a flipping board 230 at its proximal end, separated by a spring 234. Holes 212 provide fluid communication between the dry powder chamber and the external environment atmosphere 5. When the user starts to inhale, a negative pressure is generated in the air chamber 226, which starts to squeeze powder from the dry powder chamber 228. The flipping board 230 can flip back and forward. When in the convex-out position shown in FIGS. 11C and 11D, the flipping board 230 clamps the bar 239 with the spring 234 to keep it from moving. The flipping board 230 squeezes out a partial dosage of powder while the patient is inhaling. After the inhalation is complete, the flipping board becomes loose again, and releases its clamp.

Figure 12A:
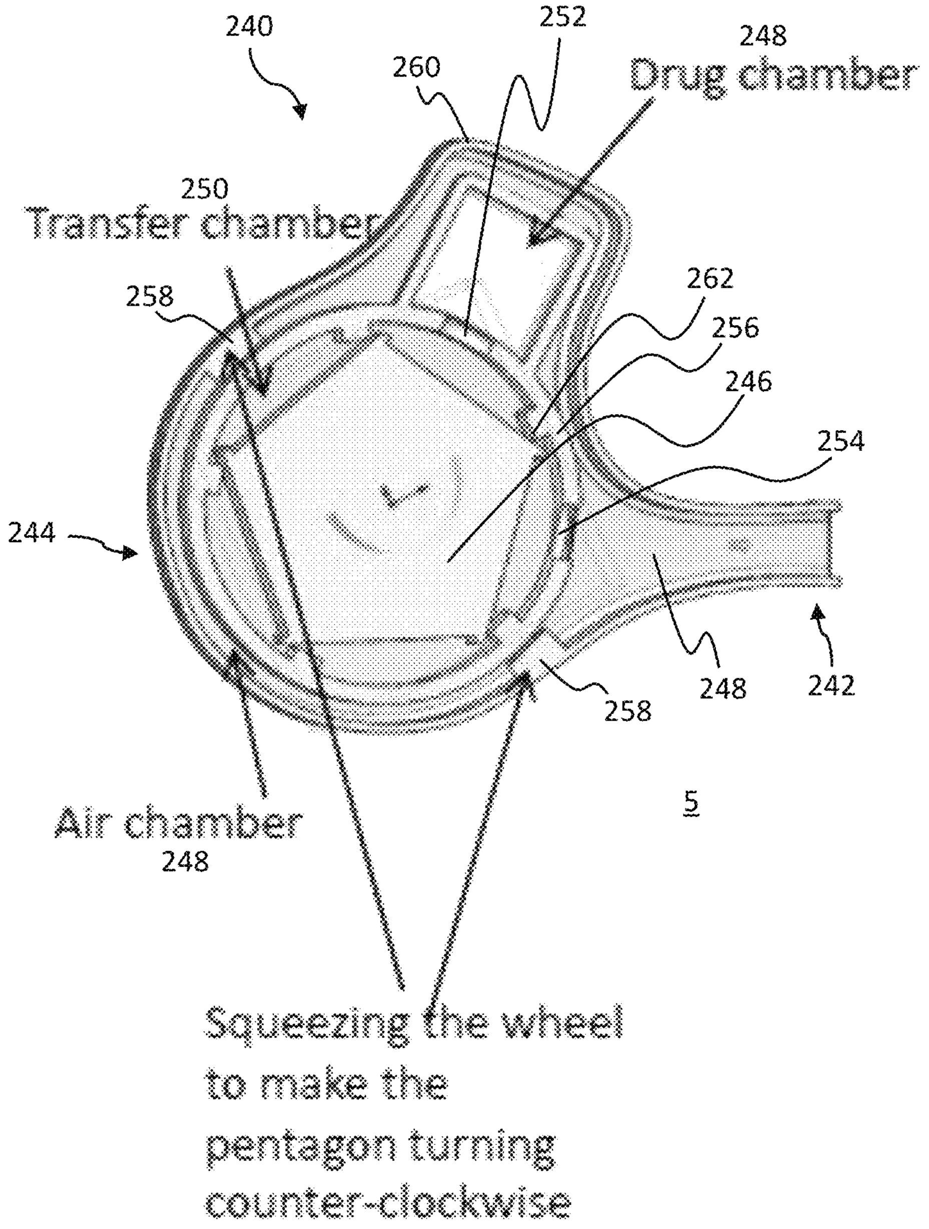
FIG. 12A is a side cutaway view of a dry powder inhaler according to an exemplary embodiment of the invention.
Figure 12B:
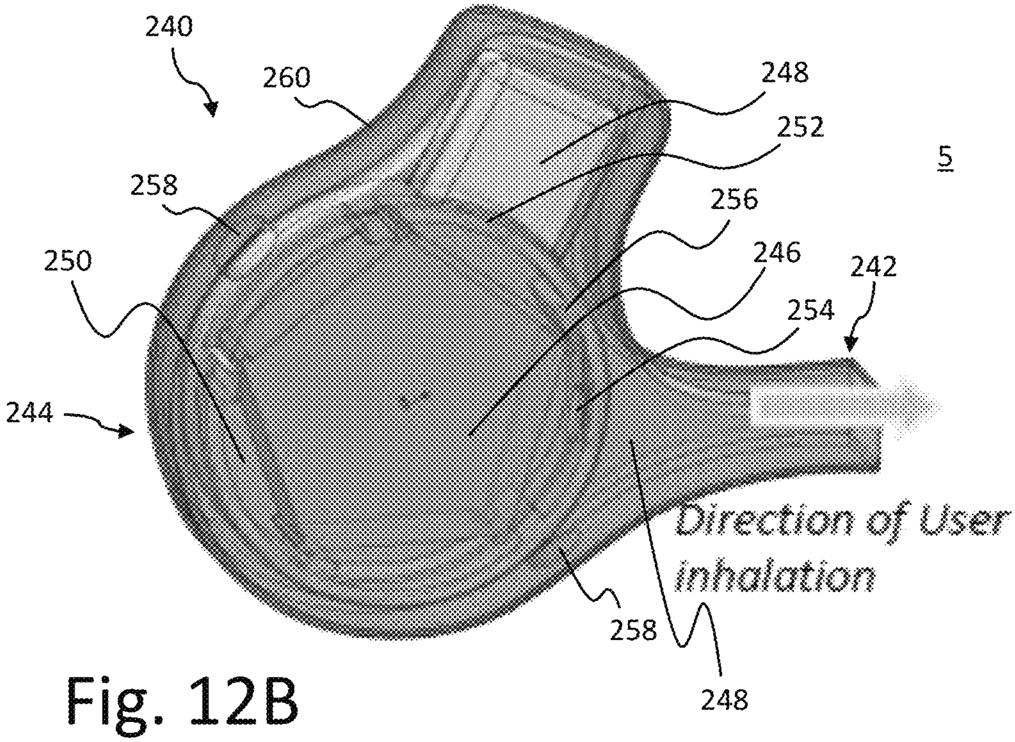
FIG. 12B is a side view of the dry powder inhaler shown in FIG. 12A.
Figure 12C:
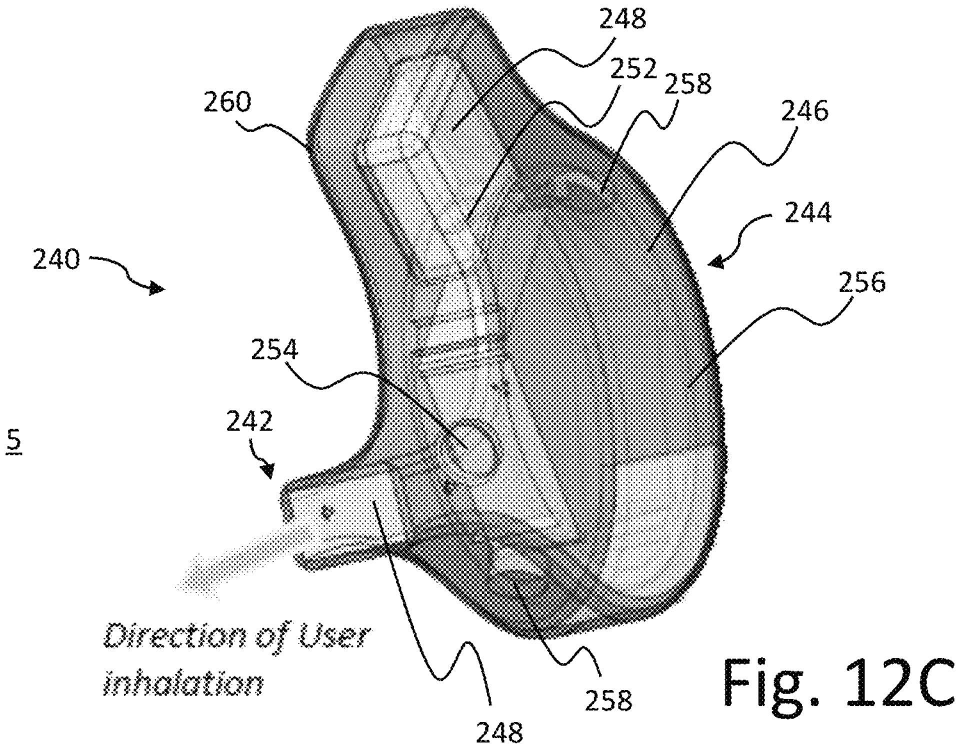
FIG. 12C is a perspective view of the dry powder inhaler shown in FIG. 12A.

In certain embodiments, a shaped component is rotated to deliver partial dosages of a powder to the air chamber. As shown in FIGS. 12A-12C, a housing 260 of the inhaler 240 has a circular component to its shape for housing a wheel 256 and a drug chamber 248. An air chamber 248 runs through portions of the housing 260, terminating in an opening at the proximal end 242 of the housing 260. The wheel 256 has a wheel opening 252 providing fluid communication between rotating transfer chambers 250 and the drug chamber 248. The wheel 256 and portions of the housing 260 are made of a semi-flexible material, such as plastic or a semi-rigid shape memory polymer. In this embodiment, a pentagon shaped component 246 is designed to fit and rotate within the wheel 256. Protrusions 262 on the inside of the wheel 256 interface with the geometry of the pentagon shaped component 246 so that in an uncompressed state, the protrusions 262 oppose corners of the pentagon shaped component 246 and restrict it from continuing to rotate past its current position. Since portions of the housing 260 and wheel 256 are semi-flexible, users can squeeze the housing 260 and wheel 256 by pressing two or more contact points 258 towards each other. Squeezing the contact points 258 temporarily distorts the shape of the wheel 256 so that the protrusions 262 allow the wheel 256 to slip by and spin counterclockwise to the next position. In certain embodiments, the interface between wheel protrusions 262 and corners of the pentagon shaped component 246 can generate an audible "click" as the corner slips past the protrusion, indicating to the user that a new transfer chamber 250 is in position at the wheel airway opening 254. In the embodiment illustrated, each flat edge of the pentagon shaped component 246 and corresponding curved edge of the wheel 256 between protrusions 262 defines the geometry of a transfer chamber 250. During operation, a user will inhale on the opening at the proximal end 242 of the housing 260, generating a negative pressure within the air chamber 248. When the inhaler 240 is being used for the first time, one or more transfer chambers 250 can be preloaded with a partial dose of powder. If, for example, the user receives an inhaler where only the transfer chamber adjacent to the wheel opening 252 contains powder, the user may be instructed to turn the pentagon shaped component 246 four "clicks" counterclockwise to put the powder in position to transfer through the wheel airway opening 254. With the powder positioned behind the wheel airway opening 254, the user can inhale through the opening at the proximal end 242 of the housing 260, inhaling the partial dose of powder medicament. Subsequent inhalations of subsequent partial dosages of powder can be taken by squeezing the housing 260 at the contact points 258, turning the pentagon shaped component 246 counterclockwise one click, and inhaling through the air chamber 248. In alternate embodiments, the pentagon shaped component 246 is another shape, such as a square, triangle, hexagon, heptagon, octagon or other regular polygon-like shape and the wheel 256 can be modified accordingly as will be appreciated by those having ordinary skill in the art.

Designs according to embodiments of the invention can be modified to approximate flow resistance and volume flow rate models determined to be comfortable to users. Valves, air inlets, chamber dimensions, mouthpiece pathways, housing dimensions, and limiting components can be designed so that the user initially pulls for about one second, similar to drag on a cigarette. Partial dosages are fluidized and deagglomerated, and enter the mouth and the upper respiratory tract of the user. After about one second, chase air can be delivered at a much lower flow resistance and is utilized as a primary source of air introduced into the system. The higher flow rate takes aerosol comfortably beyond the upper respiratory tract to the lungs.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A dry powder inhaler comprising:

a housing comprising a proximal end, a distal end, a chamber, and a protrusion protruding into the chamber; and a capsule housed inside the chamber and containing a dry powder, wherein the housing includes at least one opening in fluid communication with the chamber; and wherein the protrusion restricts movement and spin of the capsule and causes a longitudinal axis of the capsule to be skewed with a longitudinal axis of the chamber, thereby causing only a portion of the dry powder within the capsule to be released into the flow of air upon inhalation such that a full dosage of the dry powder is delivered over multiple inhalations.

2. The dry powder inhaler of claim 1, wherein at least a portion of the chamber tapers down in a distal direction.

3. The dry powder inhaler of claim 1, wherein the chamber has a circular cross-section.

4. The dry powder inhaler of claim 1, wherein the at least one chamber opening is angled.

5. The dry powder inhaler of claim 1, wherein the movement is a sliding movement.

6. The dry powder inhaler of claim 1, wherein the housing comprises a plurality of angled air inlets configured to facilitate vortex air flow.

7. The dry powder inhaler of claim 6, wherein the protrusion interrupts the vortex air flow within the chamber.

* * * * *